US008703428B2

(12) United States Patent
Fang et al.

(10) Patent No.: US 8,703,428 B2
(45) Date of Patent: Apr. 22, 2014

(54) SINGLE-CELL LABEL-FREE ASSAY

(75) Inventors: Ye Fang, Painted Post, NY (US); Ann M. Ferrie, Painted Post, NY (US); Qi Wu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 1197 days.

(21) Appl. No.: 12/128,267

(22) Filed: May 28, 2008

(65) Prior Publication Data

US 2009/0093013 A1 Apr. 9, 2009

Related U.S. Application Data

(60) Provisional application No. 60/997,908, filed on Oct. 6, 2007.

(51) Int. Cl.
G01N 33/53 (2006.01)
C12N 1/00 (2006.01)
C12N 5/00 (2006.01)
C12N 5/02 (2006.01)
G01N 33/567 (2006.01)

(52) U.S. Cl.
USPC ............ 435/7.1; 435/243; 435/325; 435/410; 436/501

(58) Field of Classification Search
USPC .................... 435/7.1, 243, 325, 410; 436/501
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 5,305,074 A | 4/1994 | Feldman | 356/345 |
| 5,738,825 A | 4/1998 | Rudigier et al. | 422/82.11 |
| 5,830,766 A | 11/1998 | Attridge et al. | 436/518 |
| 6,233,471 B1 | 5/2001 | Berner et al. | 600/345 |
| 6,340,598 B1 | 1/2002 | Herron et al. | 436/518 |
| 6,707,561 B1 | 3/2004 | Budach et al. | 356/521 |
| 6,727,071 B1 | 4/2004 | Dunlay et al. | 435/7.21 |
| 6,818,886 B2 | 11/2004 | Tiefenthaler | 250/282 |
| 6,867,869 B2 | 3/2005 | Budach et al. | 356/521 |
| 6,870,630 B2 | 3/2005 | Budach et al. | 356/521 |
| 6,893,705 B2 | 5/2005 | Thomas et al. | 428/141 |
| 6,985,664 B2 | 1/2006 | Caracci et al. | 385/130 |
| 7,064,844 B2 | 6/2006 | Budach et al. | 356/521 |
| 7,105,347 B2 | 9/2006 | Fang et al. | 435/455 |
| 7,264,973 B2 | 9/2007 | Lin et al. | 436/518 |
| 7,286,221 B2 | 10/2007 | Caracci et al. | 356/300 |
| 2002/0127565 A1 | 9/2002 | Cunningham et al. | 435/6 |
| 2002/0160534 A1 | 10/2002 | Herron et al. | 436/518 |
| 2002/0164824 A1 | 11/2002 | Xiao et al. | 436/524 |
| 2002/0168295 A1 | 11/2002 | Cunningham et al. | 422/82.05 |
| 2003/0012692 A1 | 1/2003 | Lemee et al. | 422/57 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2003/0124516 A1 | 7/2003 | Chung et al. | 435/5 |
| 2003/0138208 A1 | 7/2003 | Pawlak et al. | 385/37 |
| 2003/0194755 A1 | 10/2003 | Schnabel et al. | 435/7.23 |
| 2003/0211461 A1 | 11/2003 | Kariv et al. | 435/4 |
| 2004/0009540 A1 | 1/2004 | Soohoo et al. | 435/7.23 |
| 2004/0023310 A1 | 2/2004 | Kariv et al. | 435/7.2 |
| 2004/0033539 A1 | 2/2004 | Schnabel et al. | 435/7.21 |
| 2004/0053209 A1 | 3/2004 | Kariv et al. | 435/4 |
| 2004/0091397 A1 | 5/2004 | Picard | 422/99 |
| 2004/0132172 A1 | 7/2004 | Cunningham et al. | 435/287.2 |
| 2004/0151626 A1 | 8/2004 | Cunningham et al. | 422/58 |
| 2004/0223881 A1 | 11/2004 | Cunningham et al. | 422/82.05 |
| 2004/0235198 A1 | 11/2004 | Marx et al. | 436/527 |
| 2004/0263841 A1 | 12/2004 | Caracci et al. | 356/300 |
| 2005/0070027 A1 | 3/2005 | Gollier et al. | 436/518 |
| 2005/0100904 A1 | 5/2005 | Yoshizato et al. | 435/6 |
| 2005/0158880 A1 | 7/2005 | Ostuni et al. | 438/1 |
| 2005/0236554 A1 | 10/2005 | Fontaine et al. | 250/208.1 |
| 2006/0063276 A1 | 3/2006 | Jiang et al. | 436/518 |
| 2006/0205058 A1 | 9/2006 | Frutos et al. | 435/287.1 |
| 2006/0205092 A1 | 9/2006 | Lackritz et al. | 436/525 |
| 2006/0223051 A1 | 10/2006 | Fang et al. | 435/4 |
| 2006/0246043 A1* | 11/2006 | Inoue et al. | 424/93.21 |
| 2009/0142790 A1* | 6/2009 | Fang et al. | 435/29 |

FOREIGN PATENT DOCUMENTS

| | | |
|---|---|---|
| WO | WO 01/57530 | 8/2001 |
| WO | WO 02/08762 | 1/2002 |
| WO | WO 2004/044171 | 5/2004 |
| WO | WO 2005/005979 | 1/2005 |
| WO | WO 2005/017507 | 2/2005 |
| WO | WO 2006/107967 | 10/2006 |
| WO | WO 2006/108183 | 10/2006 |
| WO | WO 2007/015878 | 2/2007 |
| WO | WO 2007/018872 | 2/2007 |

OTHER PUBLICATIONS

Fang et al., Analytical Chemistry 77 : 5720 (2005).*
Ferrie et al., High resolution resonant waveguide grating imager for cell cluster analysis under physiological conditions. Applied Physics Letters 100 :223701 (2012).*
Z.H. Wang et al., "A Label-Free Multisensing Immunosensor Based on Imaging Ellipsometry", Anal. Chem., 2003, vol. 75, pp. 6119-6123.
C.E. Jordan et al., "Surface Plasmon Resonance Imaging Measurements of DNA Hybridization Adsorption and Streptavidin/DNA Multilayer Formation at Chemically Modified Gold Surfaces", Anal. Chem., 1997, pp. 4939-4947.
Y. Fang et al., "Characteristics of Dynamic Mass Redistribution of Epidermal Growth Factor Receptor Signaling in Living Cells Measured with Label-Free Optical Biosensors", Anal. Chem., 2005, vol. 77, pp. 5720-5725.

(Continued)

Primary Examiner — Ethan C Whisenant

(74) Attorney, Agent, or Firm — John L. Haack

(57) ABSTRACT

The disclosure provides a system and method for characterizing a single live-cell response to a stimulus with a biosensor imaging system having cells immobilized on the biosensor at a resolution level of a single cell, as defined herein.

19 Claims, 10 Drawing Sheets

(56) References Cited

OTHER PUBLICATIONS

Y. Fang et al., "Optical biosensor provides insights for bradykinin $B_2$ receptor signalling in A431 cells", *FEBS Letters*, 2005, vol. 579, pp. 6365-6374.

Y. Fang et al., "Resonant Waveguide Grating Biosensor for Living Cell Sensing", *Biophysical Journal*, Sep. 2006, vol. 91, pp. 1925-1940.

Y. Fang et al., "Non-invasive optical biosensor for assaying endogenous G protein-coupled receptors in adherent cells", *Journal of Pharmacological and Toxicological Methods*, 2007, vol. 55, pp. 314-322.

Y. Fang, "Label-Free Cell-Based Assays with Optical Biosensors in Drug Discovery", *Assay and Drug Development Technologies*, 2006, vol. 4, No. 5, pp. 583-595.

L.C. Waters et al., "Microchip Device for Cell Lysis, Multiplex PCR Amplification, and Electrophoretic Sizing", *Anal. Chem*, 1998, vol. 70, pp. 158-162.

E.A. Smith et al., "Surface Plasmon Resonance Imaging as a Tool to Monitor Biomolecular Interactions in an Array Based Format", *Applied Spectroscopy*, 2003, vol. 57, No. 11, pp. 320A-332A.

G.L. Duveneck et al., "Two-Photon Fluorescence Excitation of Macroscopic Areas on Planar Waveguides", *Biosensors and Bioelectronics*, vol. 18, 2003, pp. 503-510.

Ye Fang et al., "Cellular functions of cholesterol probed with optical biosensors", *Biochimica et Biophysica Acta*, vol. 1763, 2006, pp. 254-261.

Y. Fang et al., "Characteristics of Dynamic Mass Redistribution of Epidermal Growth Factor Receptor Signaling in Living Cells Measured with Label-Free Optical Biosensors", *Anal. Chem.*, vol. 77, 2005, pp. 5720-5725.

Y. Fang et al., "G-Protein-Coupled Receptor Microarrays", *ChemBioChem*, Oct. 4, 2002, vol. 3, No. 10, pp. 987-991.

Y. Fang, "Label-Free Cell-Based Assays with Optical Biosensors in Drug Discovery", *Assay and Drug Development Technologies*, vol. 4, No. 5, 2006, pp. 583-595.

Y. Fang et al., "Non-Invasive Optical Biosensor for Assaying Endogenous G Protein-Coupled Receptors in Adherent Cells", *Journal of Pharmacological and Toxicological Method*, vol. 55, 2007, pp. 314-322.

Y. Fang et al., "Optical biosensor differentiates signalling of endogenous $PAR_1$, and $PAR_2$ in A431 cells", *BMC Cell Biology*, 2007, vol. 8, No. 24, pp. 1-12, http://www.biomedcentral.com/1471-2121/8/24.

Ye Fang et al., "Optical Biosensor Provides Insight for Bradykinin B2 Receptor Signaling in A431 Cells", *FEBS Letters*, vol. 579, 2005, pp. 6365-6374.

Y. Fang et al., "Probing cytoskeleton modulation by optical biosensors", *FEBS Letters*, vol. 579, 2005, pp. 4175-4180.

Y. Fang et al., "Resonant Waveguide Grating Biosensor for Living Cell Sensing", *Biophysical Journal*, vol. 91, Sep. 2006, pp. 1925-1940.

I. Giaever et al., "Monitoring fibroblast behaviour in tissue culture with an applied electric field", *Proc. Natl. Acad. Sci.*, Jun. 1984, vol. 81, pp. 3761-3764.

H.M. Grandin et al., "Waveguide Excitation Fluorescence Microscoopy: A New Tool for Sensing and Imaging the Biointerface"*Biosensors and Bioelectronics*, vol. 21, 2006, pp. 1476-1482.

A. Grakoui et al., "The Immunological Synapse: A Molecular Machine Controlling T Cell Activation", *Science*, vol. 285, Jul. 9, 1999, pp. 221-227.

S.A. Green et al., "Sustained Activation of a G Protein-coupled Receptor via "Anchored" Agonist Binding", *The Journal of Biological Chemistry*, vol. 271, No. 39, pp. 24029-24035.

M. Halter et al., "Enhanced Optical Waveguide Light Mode Spectroscopy Via Detection of Fluorophore Absorbance", *Review of Scientific Instruments*, vol. 77, 2006, pp. 103105-1-6.

M. Hide et al., "Real-Time Analysis of Ligand-Induced Cell Surface and Intracellular Reactions of Living Mast Cells Using a Surface Plasmon Resonance-Based Biosensor", *Analytical Biochemistry*, vol. 302, 2002, pp. 28-37.

K. Solly et al., "Application of Real-Time Cell Electronic Sensing (RT-CES) Technology to Cell-Based Assays", *ASSAY and Drug Development Technologies*, 2004, vol. 2, No. 4, pp. 363-372.

G. Swaminath et al., "Probing the $\beta_2$ Adrenoceptor Binding Site with Catechol Reveals Differences in Binding and Activation by Agonists and Partial Agonists", *The Journal of Biological Chemistry*, vol. 280, No. 23, pp. 22165-22171.

Tiefenthaler et al., "Intregrated Optical Switches and Gas Sensors", *Optics Letters*, Apr. 1984, vol. 10, No. 4, pp. 137-139.

J.D. Urban et al., "Functional Selectivity and Classical Concepts of Quantitative Pharmacology", *The Journal of Pharmacology and Experimental Therapeutics*, vol. 320, No. 1, pp. 1-13.

E. Verdonk et al., "Cellular Dielectric Spectroscopy: A Label-Free Comprehensive Platform for Functional Evaluation of Endogenous Receptors", *ASSAY and Drug Development Technologies*, 2006, vol. 4, No. 5, pp. 609-619.

G. Voirin et al., "$Si_3N_4/SiO_2$/Si Waveguide Grating for Fluorescent Biosensors", *Proc. SPIE*, vol. 3620, 1999, pp. 109-116.

J. Vörös et al., "Optical Grating Coupler Biosensors", *Biomaterials*, vol. 23, 2002, pp. 3699-3710.

Z.H. Wang et al. "A Label-Free Multisensing Immunosensor Based on Imaging Ellipsometry", *Anal. Chem.*, 2003, vol. 75, pp. 6119-6123.

L.C. Waters et al., "Microchip Device for Cell Lysis, Multiplex PCR Amplification, and Electrophoretic-Sizing", *Anal. Chem.*, 1998, vol. 70, pp. 158-162.

P.N. Zeller et al., "Single-Pad Scheme for Integrated Optical Fluorescence Sensing", *Biosensors & Bioelectronics*, vol. 15, 2000, pp. 591-595.

"Zeptosens—Bioanalytical Solutions", http://www.zeptosens.com/en/.

D.R. Alessi et al., "PD 098059 Is a Specific Inhibitor of the Activation of Mitogen-activated Protein Kinase Kinase in Vitro and in Vivo", *The Journal of Biological Chemistry*, Nov. 17, 1995, vol. 270, No. 46, pp. 27489-27494.

M. Azzi et al., "β-Arrestin-mediated activation of MAPK by inverse agonists reveals distinct active conformations for G protein-coupled receptors", *PNAS*, Sep. 30, 2003, vol. 100, No. 20, pp. 11406-11411.

Z. Bajzer et al., "Binding, Internalization, and Intracellular Processing of Proteins Interacting with Recycling Receptors", *The Journal of Biological Chemistry*, Aug. 15, 1989, vol. 264, No. 23, pp. 13623-13631.

J.G. Baker et al., "Influence of Agonist Efficacy and Receptor Phosphorylation on Antagonsit Affinity Measurements: Differences between Second Messenger and Reporter Gene Responses", *Mol. Pharmacol.*, 2003, vol. 64, No. 3, pp. 679-688.

D.W. Barnes, "Epidermal Growth Factor Inhibits Growth of A431 Human Epidermoid Carcinoma in Serum-free Cell Culture", *The Journal of Cell Biology*, Apr. 1982, vol. 93, pp. 1-4.

O. Beske et al., "A Novel Encoded Particle Technology that Enables Simultaneous Interrogation of Multiple Cell Types", *The Society of Biomolecular Screening*, 2004, vol. 9, No. 3, pp. 173-185.

Brecht et al., "Optical Probes and Transducers*", *Biosensors and Bioelectronics*, vol. 10, pp. 923-936.

W. Budach et al., "Planar Waveguides as High-Performance Sensing Platforms for Fluorescence-Based Multiplexed Oligonucleotide Hybridization Assays", *Anal. Chem.*, 1999, vol. 71, pp. 3347-3355.

P. Burke et al., "Regulation of Epidermal Growth Factor Receptor Signaling by Endocytosis and Intracellular Trafficking", *Molecular Biology of the Cell*, Jun. 2001, vol. 12, pp. 1897-1910.

K. Choudhuri et al., "T-cell receptor triggering is critically dependent on the dimensions of its peptide-MHC ligand", *Nature*, vol. 436, Jul. 28, 2005, pp. 578-582.

Clere et al., "Direct Immunosensing With an Integrated-Optical Output Grating Coupler", *Sensors & Actrators B.* vol. 40, 1997, pp. 53-58.

B. Cunningham et al., "Label-Free Assays on the BIND System", *The Society for Biomolecular Screening*, 2004, vol. 9, No. 6, pp. 481-490.

Y. Danjo et al., "Actin "purse string" filaments are anchored by E-cadherin-mediated adherens junctions at the leading edge of the epithelial wound, providing coordinated cell movement", *Journal of Cell Science*, 1998, vol. 111, pp. 3323-3331.

(56) References Cited

OTHER PUBLICATIONS

R.J. Daly, "Take Your Partners, Please—Signal Diversification by the erbB Family of Receptor Tyrosine Kinases", Growth Factors, vol. 16, pp. 255-263.
H. Daub et al., "Role of transactivation of the EGF receptor in signalling by G-protein-coupled receptors", Nature, Feb. 8, 1996, vol. 379, pp. 557-560.
Drews, "Drug Discovery: A Historical Perspective", Science, Mar. 17, 2000, vol. 287, pp. 1960-1964.
G.L. Duveneck et al., "Novel Bioaffinity Sensors for Trace Analysis Based on Luminescence Exitation by Planar Waveguides", Sensors and Actuators B, vol. 38-39, 1997, pp. 88-95.
G.L. Duveneck et al., "Review on Fluorescence-Based Planar Waveguide Biosensors", Proc. SPIE, vol. 3858, 1999, pp. 59-71.
P.L. Edmiston et al., "Dipole Orientation Distributions in Langmuir—Blodgett Films by Planar Waveguide Linear Dichroism and Fluorescence Anisotropy", J. Phys. Chem., 1996, vol. 100, pp. 775-784.
Ye Fang et al., "Cellular functions of cholesterol probed with optical biosensors", Biochimica et Biophysica Acta, vol. 1763, 2006, pp. 254-261.
Y. Fang et al., "Characteristics of Dynamic Mass Redistribution of Epidermal Growth Factor Receptor Signaling in Living Cells Measured with Label Free Optical Biosensors", Anal. Chem., vol. 77, 2005, pp. 5720-5725.
Y. Fang et al., "Optical biosensor differentiates signalling of endogenous $PAR_1$, and $PAR_2$ in A431 cells", BMC Cell Biology, 2007, vol. 8, No. 24, pp. 1-12, http://www.biomedcentral.com/1471-2121/8/24.
Ye Fang et al., "Optical Biosensor Provides Insights for Bradykinin B2 Receptor Signaling in A431 Cells", FEBS Letters, vol. 579, 2005, pp. 6365-6374.
A.R. French et al., "Postendocytic Trafficking of Epidermal Growth Factor-Receptor Complexes Is Mediated Through Saturable and Specific Endosomal Interactions", The Journal of Biological Chemistry, Jun. 3, 1994, vol. 269, No. 22, pp. 15749-15755.
A. Glading et al., "Epidermal Growth Factor Receptor Activation of Calpain Is Required for Fibroblast Motility and Occurs via an ERK/MAP Kinase Signaling Pathway", The Journal of Biological Chemistry, Jan. 28, 2000, vol. 275, No. 4, pp. 2390-2398.
H.M. Grandin et al., "Waveguide Excitation Fluorescence Microscopy: A New Tool for Sensing and Imaging the Biointerface", Biosensors and Bioelectronics, vol. 21, 2006, pp. 1476-1482.
A. Graness et al., "Protein-tyrosine-phosphatase-mediated epidermal growth factor (EGF) receptor traninactivation and EGF receptor-independent stimulation of mitogen-activated protein kinase by bradykinin in A431 cells", Biochem. J., vol. 347, pp. 441-447.
A. Grakoui et al., "The Immunological Synapse. A Molecular Machine Controlling T Cell Activation", Science, vol. 285, Jul. 9, 1999, pp. 221-227.
S.A. Green et al., "Sustained Activation of a G Protein-coupled Receptor via "Anchored" Agonist Binding", The Journal of Biological Chemistry, vol. 271, No. 39, pp. 24029-24035.
A. Gschwind et al., "Cell communication networks: epidermal growth factor receptor transactivation as the paradigm for interrreceptor signal transmission", Oncogene, 2001, vol. 20, pp. 1594-1600.
M. Halter et al., "Enhanced Optical Waveguide Light Mode Spectroscoopy Via Detection of Fluorophore Absorbance", Review of Scientific Instruments, vol. 77, 2006, pp. 103105-1-6.
W.R. Holland et al., "Waveguide Mode Enhancement of Molecular Fluorescence", Optics Letters, vol. 10, No. 8, Aug. 1985, pp. 414-416.
R. Horváth et al., "Effect of patterns and inhomogeneities on the surface of waveguides used for optical waveguide lightmode spectroscopy applications", Applied Physics B, 2001, vol. 72, pp. 441-447.
R. Harváth et al., "Reverse-symmetry waveguides: theory and fabrication", Applied Physics B, vol. 74, pp. 383-393.

Y. Huang et al., "Growth Hormone-induced Phosphorylation of Epidermal Growth Factor (EGF) Receptor in 3T3-F442A Cells", The Journal of Biological Chemistry, May 23, 2003, vol. 278, No. 21, pp. 18902-18913.
W. Huber et al., "Direct optical immunosensing (sensitivity and selectivity)", Sensors and Actuators B, 1992, vol. 6, pp. 122-126.
B. January et al., "$\beta_2$-Adrenergic Receptor Desensitization, Internationalization, and Phosphorylation in Response to Full and Partial Agonists", The Journal of Biological Chemistry, vol. 272, No. 38, pp. 23871-23879.
Jin et al., "A Biosensor Concept Based on Imaging Ellipsometry for Visualization of Biomolecular Interactions", Analytical Biochemistry, vol. 232, 1995, pp. 69-72.
C.E. Jordan et al., "Surface Plasmon Resonance Imaging Measurements, of DNA Hybridization Adsorption and Streptavidin/DNA Multilayer Formation at Chemically Modified Gold Surfaces", Anal. Chem., 1997, pp. 4939-4947.
Jordan et al., "Surface Plasmon Resonance Imaging Measurements of Electrostatic Biopolymer Adsorption Onto Chemically Modified Gold Surfaces", Anal. Chem., 1997, vol. 69, pp. 1449-1456.
P. Lalanne et al., "Highly Improved Convergence of the Coupled-Wave Method for TM Polarization", J. Opt. Soc. Am. A, vol. 13, No. 4, Apr. 1996, pp. 779-784.
M.A. Lemmon et al., "Regulation of signal transduction and signal diversity by receptor oligomerization", Trends Biochem. Sci., 1994, vol. 19, pp. 459-463.
G. Liapakis et al., "Synergistic Contributions of the Functional Groups of Epinephrine to Its Affinity and Efficacy at the $\beta_2$ Adrenergic Receptor", Mol. Pharmacol., 2004, vol. 65, No. 5, pp. 1181-1190.
G. Liapakis et al., "The Forgotten Serine", The Journal of Biological Chemistry, vol. 275, No. 48, pp. 37779-37788.
Y. Liu et al., "Structural basis for selective inhibition of Src family kinases by PP1", Chemistry & Biology, 1999, vol. 6, No. 9, pgs. 671-678.
E. Livneh et al., "Reconstitution of Human Epidermal Growth Factor Receptors and Its Deletion Mutants in Cultured Hamster Cells", The Journal of Biological Chemistry, Sep. 25, 1986, vol. 261, No. 27, pp. 12490-12497.
L. Lorenzelli, et al., "Bioelectrochemical signal monitoring of in-vitro cultured cells by means of an automated microsystem based on solid state sensor-array", Biosensors and Bioelectronics, 2003, vol. 18, pp. 621-626.
Z. Lu et al., "Epidermal Growth Factor-Induced Tumor Cell Invasion and Metastasis Initiated by Dephosphorylation and Downregulation of Focal Adhesion Kinase", Molecular and Cellular Biology, Jun. 2001, vol. 21, No. 12, pp. 4016-4031.
Ma et al., "From the Analyst's Couch Value of Novelty?", Nature Reviews, Drug Discovery, vol. 1, Aug. 2002, pp. 571-572.
Morhard et al., "Immobilization of Antibodies in Micropatterns for Cell Detection by Optical Diffraction", Sensors and Actuators B, vol. 70, 2000, pp. 232-242.
K. Mossman et al., "Micropatterned supported membranes as tools for quantitative studies of the immunological synapse", Chemical Society Reviews, vol. 36, 2007, pp. 46-54.
B.S. Negrutskii et al., "A sequestered pool of aminoacyl-tRNA in mammalian cells", Proc. Natl. Acad. Sci. USA, 1992, vol. 89, pp. 3601-3604.
B.S. Negratskii et al., "Supramolecular organization of the mammalian translation system", Proc. Natl. Acad. Sci. USA, 1994, vol. 91, pp. 964-968.
P.M. Nellen et al., "Integrated Optical Input Grating Couplers as Biochemical Sensors", Sensors and Actuators, 1988, vol. 15, pp. 285-295.
Y. Nong et al., "Glycine binding primes NMDA receptor internalization", Nature, Mar. 20, 2003, vol. 422, pp. 302-307.
Pierce et al., "Seven Transmembrane Receptors", Nature Reviews, Molecular Cell Biology, vol. 3, Sep. 2002, pp. 639-650.
G. Powis et al., "Wortmannin, a Potent and Selective Inhibitor of Phosphatidylinositol-3-kinase", Cancer Research, May 1, 1994, vol. 54, pp. 2419-2423.

(56) References Cited

OTHER PUBLICATIONS

Ramsden et al., "Kinetics of Adhesion and Spreading of Animal Cells", *Biotechnology and Bioengineering*, vol. 43, 1994, pp. 939-945.

H. Resat et al., "An Integrated Model of Epidermal Growth Factor Receptor Trafficking and Signal Transduction", *Biophysical Journal*, Aug. 2003, vol. 85, pp. 730-743.

C. Rosette et al., "Ultraviolet Light and Osmotic Stress: Activation of the JNK Cascade Through Multiple Growth Factor and Cytokine Receptors", *Science*, Nov. 15, 1996, vol. 274, pp. 1194-1197.

M.D. Salik et al., Resonant Excitation Analysis of Waveguide Grating Couplers, *Optics Communications*, vol. 193, Jun. 15, 2001, pp. 127-131.

J. Schlessinger, "Cell Signaling by Receptor Tyrosine Kinases", *Cell*, Oct. 13, 2000, vol. 103, pp. 211-225.

B. Schoeber et al., "Computational modelling of the dynamics of the MAP kinase cascade activated by surface and internalized EGF receptors", *Nature Biotechnology*, Apr. 2002, vol. 20, pp. 370-375.

M.A. Simmons, "Functional Selectivity, Ligand-Directed Trafficking, Conformation-Specific Agonism: What's In A Name?", *Molecular Interventions*, Jun. 2005, vol. 5, Issue 3, pp. 154-157.

"Signal Pathway Identification and Deconvolution", http://www.cellkey.com/apps2.html.

E.A. Smith et al., "Surface Plasmon Resonance Imaging as a Tool To Monitor Biomolecular Interactions in an Array Based Format", *Applied Spectroscopy*, 2003, vol.57, No. 11, pp. 320A-332A.

K. Tiefenthaler et al., "Sensitivity of grating couplers as integrated-optical chemical sensors", *J. Opt. Soc. Am. B*, Feb. 1989, vol. 6, No. 2, pp. 209-220.

P.K. Tien, "Integrated ooptics and new wave phenomena in optical waveguides", *Reviews of Modern Physics*, Apr. 1977, vol. 49, No. 2, pp. 361-454.

J.D. Urban et al., "Functional Selectivity and Classical Concepts of Quantitative Pharmocology". *The Journal of Pharmacology and Experimental Therapeutics*, vol. 320, No. 1, pp. 1-13.

E. Verdonk et al., "Cellular Dielectric Spectroscooopy: A Label-Free Comprehensive Platform for Functional Evaluation of Endogenous Receptors", *ASSAY and Drug Development Technologies*, 2006, vol. 4, No. 5, pp. 609-619.

P.J. Verveer, et al., "Quantitative Imaging of Lateral ErbB1 Receptor Signal Propagation in the Plasma Membrane", *Science*, Nov. 24, 2000, vol. 290, pp. 1567-1570.

J. Vörös et al., "Feasibility study of an online toxicological sensor based on the optical waveguide technique", *Biosensor & Bioelectronics*, 2000, vol. 15, pp. 423-429.

L.C. Waters et al., "Microchip Device for Cell Lysis, Multiplex PCR Amplification, and Electrophoretic Sizing", *Anal. Chem.*, 1998, vol. 70, pp. 158-162.

R. Wetzker et al., "Transactivation joins multiple tracks to the ERK/MAPK cascade", *Nature Reviews Molecular Cell Biology*, Aug. 2003, vol. 4, pp. 651-657.

A.D. Zechnich et al., "Possible Interactions With Terfenadine or Astemizole", *West J. Med.*, Apr. 1994, vol. 160, No. 4, pp. 321-325.

Brecht et al., "Optical Probes and Transducers*", *Biosensors and Bioelectronics*, vol. 10, 1995, pp. 923-936.

Clerc et al., "Direct Immunosensing With an Integrated-Optical Output Grating Coupler", Sensors & Actuators B, vol. 40, 1997, pp. 53-58.

G.L. Duveneck et al., "Novel Bioaffinity Sensors for Trace Analysis Based on Luminescence Excitation by Planar Waveguides", *Sensors and Actuators B*, vol. 38-39, 1997, pp. 88-95.

G.L. Duveneck et al., "Two-Photon fluorescence Excitation of Macroscopic Areas on Planar Waveguides", *Biosensors ana Bioelectronics*, vol. 18, 2003, pp 503-510.

Y. Fang, "Label-Free Cell-Based Assays with Optical Biosensors in Drug Discovery", *Assay and Drug Development Technologies* vol. 4, No. 5, 2006, pp. 583-595.

Y. Fang et al., "Non-Invasive Optical Biosensor for Assaying Endogenous G Protein-Coupled Receptors in Adherent Cells", *Journal of Pharmacological and Taxicological Method*, vol. 55, 2007, pp. 314-322.

Y. Fang et al., "Optical biosensor differentiates signalling of endogenous $PAR_1$, and $PAR_2$ in A431 cells", *BMC Cell Biology*, 2007; vol. 8, No. 24, pp. 1-12, http://www.biomedcentral.com/1471-2121/8/24.

Ye Fang et al., "Optical Biosensor Provides Insights for Bradykinin B2 Receptor Signaling in A431 Cells", *FEBS Letters*, vol. 579, 2005, pp. 6365-6374.

B. January et al., "$\beta_2$-Adrenergic Receptor Desensitization, Internationalization, and Phosphorylation in Response to Full and Partial Agonists", *The Journal of Biological Chemistry*, vol. 272, No. 38, pp. 23871-23879.

G.E. Jordan et al. "Surface Plasmon Resonance Imaging Measurements of DNA Hybridization Adsorption and Streptavidin/DNA Multilayer Formation at Chemically Modified Gold Surfaces", *Anal. Chem.*, 1997, pp. 4939-4947.

G. Liapakis et al., "Synergistic Contributions of the Functional Groups of Epinephrine to Its Affinity and Efficacy at the $\beta_2$ Adrenergic Receptor", *Mol. Pharmacol.*, 2004, vol. 65, No. 5, pp. 1181-1190.

Ma et al., "From the Analyst's Couch: Value of Novelty?", *Nature Reviews, Drug Discovery*, vol. 1, Aug. 2002, pp. 571-572.

Morhard et al., "Immobilization of Antibodies in Micropatterns for Cell Detection by Optical Diffraction", *Sensors and Actuators B*, vol. 70, 2000, pp. 232-242.

Pierce et al., "Seven-Transmembrane Receptors", *Nature Reviews, Molecular Cell Biology*, vol. 3, Sep. 2002, pp. 639-650.

E.A. Smith et, al., "Surface Plasmon Resonance Imaging as a Tool to-Monitor Biomoleculat Interactions in an Array Based Format" *Applied Spectroscopy*, 2003, vol. 57, No. 11, pp. 320A-332A.

J.D. Urban et al., "Functional Selectivity and Classical Concepts of Quantitative Pharmacology", *The Journal of Pharmacology ana Experimental Therapeutics*, vol. 320, No. 1, pp. 1-13.

"Zeptosens—Bioanalytical Solutions",http://www.zeptosens.com/en/.

Notice of Rejection issued Dec. 4, 2012 in corresponding Japanese Patent Application No. 2010-527986.

\* cited by examiner

FIG. 4A
FIG. 4B
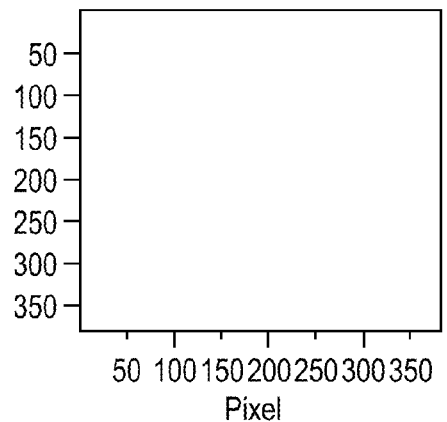
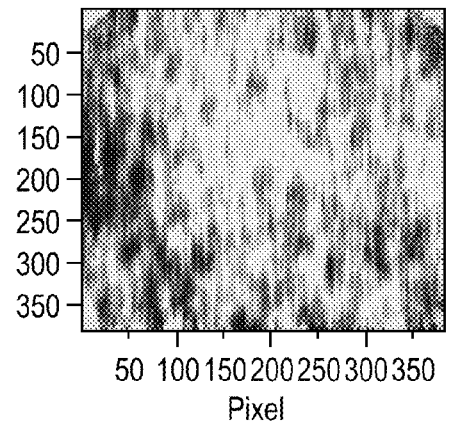
FIG. 5A
FIG. 5B
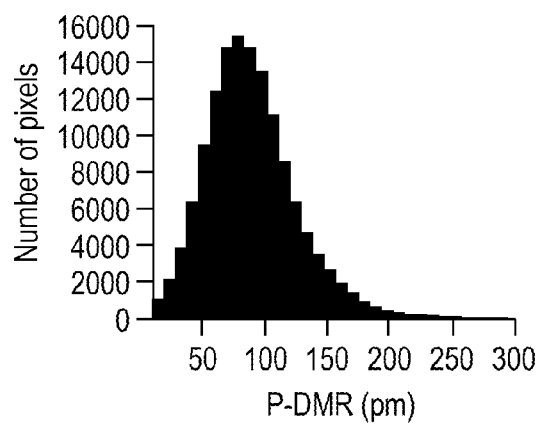
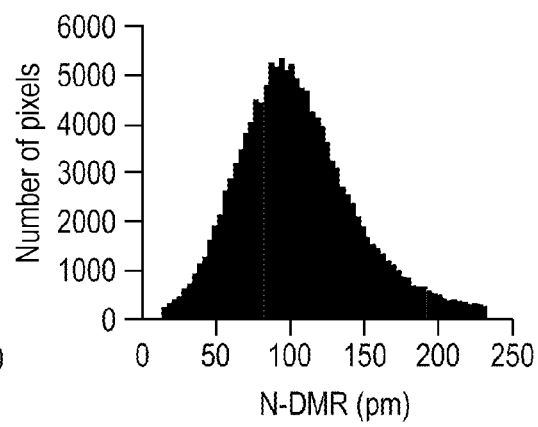

us 8,703,428 B2

SINGLE-CELL LABEL-FREE ASSAY

CLAIMING BENEFIT OF PRIOR FILED U.S. APPLICATION

This application claims the benefit of U.S. Provisional Application Ser. No. 60/997,908, filed on Oct. 6, 2007. The content of this document and the entire disclosure of publications, patents, and patent documents mentioned herein are incorporated by reference.

BACKGROUND

The disclosure relates to the field of optical biosensors, specifically resonant waveguide grating (RWG) biosensors for non-invasive single-cell analysis. The disclosure also relates to a method for accomplishing a label-free single-cell assay, which assay can be accomplished with a biosensor.

SUMMARY

The disclosure provides methods for characterizing a live-cell response to a stimulus using a biosensor imaging system effectively having the equivalent of a single live-cell immobilized on the biosensor's surface. The coordination between the biosensor interrogation and the image analysis components of the system along with the controlled immobilized cell density on the biosensor surface permits information extraction regarding the effects of a stimulus at the single-cell or sub-single-cell level.

BRIEF DESCRIPTION OF THE DRAWINGS

FIGS. 4A and 4B, respectively, show sequential resonant wavelength images, before and after stimulation with 32 nM epidermal growth factor, of an entire biosensor having a layer of quiescent A431 cells at about 100% confluency, in embodiments of the disclosure.

FIGS. 5A and 5B, respectively, show the distribution of P-DMR amplitudes and N-DMR amplitudes, respectively, of quiescent A431 cell responses upon stimulation with 32 nM EGF, in embodiments of the disclosure.

DETAILED DESCRIPTION

Figure 1:
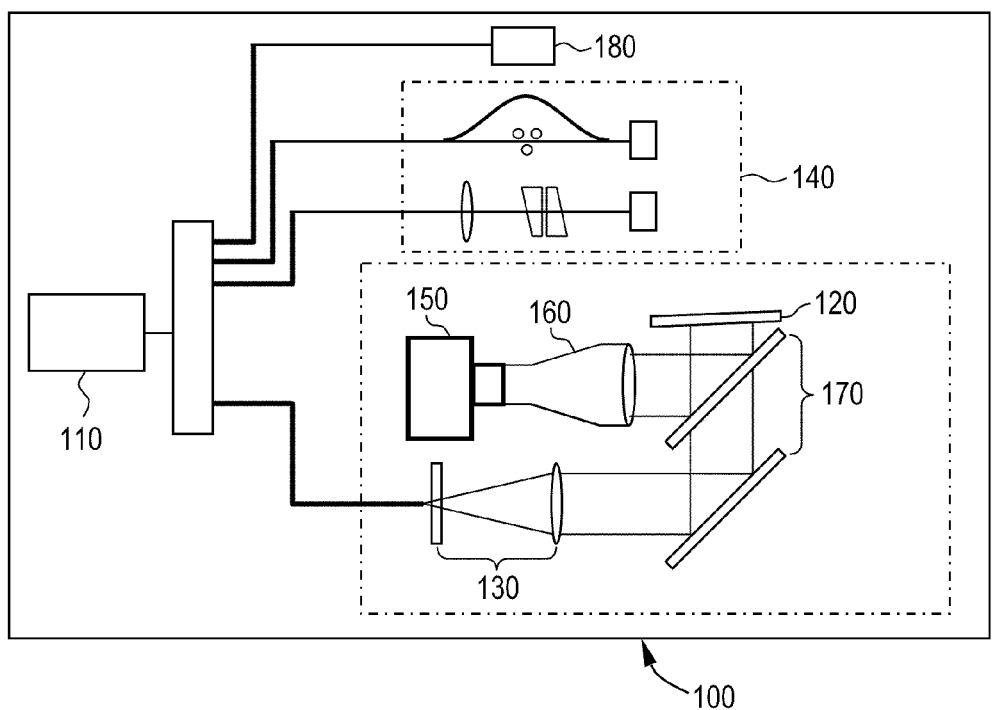
FIG. 1 illustrates an exemplary optical biosensor imaging system, in embodiments of the disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Definitions

"Assay," "assaying" or like terms refers to an analysis to determine, for example, the presence, absence, quantity, extent, kinetics, dynamics, or type of a cell's optical response upon stimulation with an exogenous stimuli, such as a ligand candidate compound or a viral particle or a pathogen.

"Attach," "attachment," "adhere," "adhered," "adherent," "immobilized", or like terms generally refer to immobilizing or fixing, for example, a surface modifier substance, a compatibilizer, a cell, a ligand candidate compound, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting with cell anchoring materials, compatibilizer (e.g., fibronectin, collagen, lamin, gelatin, polylysine, etc.), or both.

"Adherent cells" refers to a cell or a cell line or a cell system, such as a prokaryotic or eukaryotic cell, that remains associated with, immobilized on, or in certain contact with the outer surface of a substrate. Such type of cells after culturing can withstand or survive washing and medium exchanging process, a process that is prerequisite to many cell-based assays. "Weakly adherent cells" refers to a cell or a cell line or a cell system, such as a prokaryotic or eukaryotic cell, which weakly interacts, or associates or contacts with the surface of a substrate during cell culture. However, these types of cells, for example, human embryonic kidney (HEK) cells, tend to dissociate easily from the surface of a substrate by physically disturbing approaches such as washing or medium exchange. "Suspension cells" refers to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" not only refers to the culturing of cells derived from multicellular eukaryotes, especially animal cells, but also the culturing of complex tissues and organs.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of more than one type of cells (or differentiated forms of a single type of cell), which interact with each other, thus performing a biological or physiological or pathophysiological function. Such cell system includes an organ, a tissue, a stem cell, a differentiated hepatocyte cell, or the like.

"Detect" or like terms refer to an ability of the apparatus and methods of the disclosure to discover or sense a stimulus-induced cellular response and to distinguish the sensed responses for distinct stimuli.

"Pathogen" or like terms refer to, for example, a virus, a bacterium, a prion, and like infectious entities, or combinations thereof.

"Stimulus," "therapeutic candidate compound," "therapeutic candidate," "prophylactic candidate," "prophylactic agent," "ligand candidate," or like terms refer to a molecule or material, naturally occurring or synthetic, which is of interest for its potential to interact with a cell attached to the biosensor. A therapeutic or prophylactic candidate can include, for example, a chemical compound, a biological molecule, a peptide, a protein, a biological sample, a drug candidate small molecule, a drug candidate biologic molecule, a drug candidate small molecule-biologic conjugate, and like materials or molecular entity, or combinations thereof, which can specifically bind to or interact with at least one of a cellular target or a pathogen target such as a protein, DNA, RNA, an ion, a lipid or like structure or component of a living cell.

"Biosensor" or like terms refer to a device for the detection of an analyte that combines a biological component with a physicochemical detector component. The biosensor typically consists of three parts: a biological component or element (such as tissue, microorganism, pathogen, cells, or combinations thereof), a detector element (works in a physicochemical way such as optical, piezoelectric, electrochemical, thermometric, or magnetic), and a transducer associated with both components. The biological component or element can be, for example, a living cell, a pathogen, or combinations thereof. In embodiments, an optical biosensor can comprise an optical transducer for converting a molecular recognition or molecular stimulation event in a living cell, a pathogen, or combinations thereof into a quantifiable signal.

"Epidermal growth factor" or "EGF" refers to a growth factor that plays a significant role in the regulation of cell growth, proliferation and differentiation. Human EGF is a 6,045 Da protein with 53 amino acid residues and three intramolecular disulfide bonds. EGF acts by binding with high affinity to epidermal growth factor receptor (EGFR) on the cell surface and stimulating the intrinsic protein-tyrosine kinase activity of the receptor. The tyrosine kinase activity in turn initiates a signal transduction cascade which results in a variety of biochemical changes within the cell, such as, a rise in intracellular calcium levels, increased glycolysis and protein synthesis, and increases in the expression of certain genes including the gene for EGFR that ultimately lead to DNA synthesis and cell proliferation.

"Epidermal growth factor receptor" or "EGFR" or like terms refers to a particular receptor on the cell's surface that can be activated by binding of its specific ligands, including epidermal growth factor (EGF) and transforming growth factor α (TGFα). The epidermal growth factor receptor (EGFR) is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). The related ErbB-3 and ErbB-4 receptors are activated by neuregulins (NRGs). ErbB-2 has no known direct activating ligand, and may be in an activated state constitutively. Upon activation by its growth factor ligands, EGFR undergoes a transition from an inactive monomeric form to an active homodimer, although there is some evidence that preformed inactive dimers may also exist before ligand binding. In addition to forming homodimers after ligand binding, EGFR may pair with another member of the ErbB receptor family, such as ErbB2/Her2/neu, to create an activated heterodimer. There is also evidence to suggest that clusters of activated EGFRs form, although it is unclear whether this clustering is important for activation itself or occurs subsequent to activation of individual dimers.

G protein-coupled receptors (GPCRs) are also known as seven transmembrane receptors, 7TM receptors, heptahelical receptors, and G protein linked receptors (GPLR). GPCRs are a large protein family of transmembrane receptors that sense molecules outside the cell and activate inside signal transduction pathways and, ultimately, cellular responses. The ligands that bind and activate these receptors include light-sensitive compounds, odors, pheromones, hormones, and neurotransmitters, and vary in size from small molecules to peptides to large proteins. GPCRs are involved in many diseases, but are also the target of around half of all modern medicinal drugs. GPCRs can be grouped into 4 classes based on sequence homology and functional similarity: Class A rhodopsin-like, Class B secretin-like, Class C metabotropic/pheromone, and Class D Fungal pheromone. GPCRs are involved in a wide variety of physiological processes, including the visual sense, the sense of smell, behavioral and mood regulation, regulation of immune system activity and inflammation, autonomic nervous system transmission, cell density sensing, and many others. GPCRs include receptors for sensory signal mediators (e.g., light and olfactory stimulatory molecules); adenosine, bombesin, bradykinin, endothelin, γ-aminobutyric acid (GABA), hepatocyte growth factor, melanocortins, neuropeptide Y, opioid peptides, opsins, somatostatin, tachykinins, vasoactive intestinal polypeptide family, and vasopressin; biogenic amines (e.g., dopamine, epinephrine and norepinephrine, histamine, glutamate (metabotropic effect), acetylcholine (muscarinic effect), and serotonin); chemokines; lipid mediators of inflammation (e.g., prostaglandins and prostanoids, platelet activating factor, and leukotrienes); and peptide hormones (e.g., calcitonin, C5a anaphylatoxin, follicle stimulating hormone (FSH), gonadotropic-releasing hormone (GnRH), neurokinin, and thyrotropin releasing hormone (TRH), and oxytocin). GPCRs which act as receptors for stimuli that have yet to be identified are known as orphan receptors. It is known that the inactive G protein is bound to the receptor in its inactive state. Once the ligand is recognized, the receptor shifts conformation and thus mechanically activates the G protein, which detaches from the receptor. The receptor can now either activate another G protein, or switch back to its inactive state. This is an overly simplistic explanation, but suffices to convey the overall set of events. It is believed that a receptor molecule exists in a conformational equilibrium between active and inactive biophysical states. The binding of ligands to the receptor may shift the equilibrium toward the active receptor states. Three types of ligands exist: agonists are ligands which shift the equilibrium in favor of active states; inverse agonists are ligands which shift the equilibrium in favor of inactive states; and neutral antagonists are ligands which do not affect the equilibrium. It is not yet known how exactly the active and inactive states differ from each other. A GPCR can mediate both G protein-dependent and independent signaling, often in a ligand-dependent manner.

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

"Consisting essentially of" in embodiments refers, for example, to a surface composition, a method of making or using a surface composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, decreased affinity of the cell for the biosensor surface, aberrant affinity of a stimulus for a cell surface receptor or for an intracellular receptor, anomalous or contrary cell activity in response to a ligand candidate or like stimulus, and like characteristics.

Thus, the claimed invention may suitably comprise, consist of, or consist essentially of: a method for characterizing a live-cell response to a stimulus as defined herein.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, ingredients, additives, cell types, antibodies, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

In embodiments, the disclosure provides a method for characterizing nominalized single live-cell response to a stimulus, the method comprising:

providing a biosensor imaging system having a cell immobilized on a biosensor;

contacting the immobilized cells with a stimulus for a selected cellular target for a period of time;

detecting the dynamic mass redistribution of the contacted cells with the biosensor at a single cell, a sub-single cell, or a single clustered cell level; and determining the difference effect of the stimulus on the cell-signaling of the cellular target.

The period of time can comprise, for example, at least one of from about seconds to about minutes, from about minutes to about hours, from about days to about weeks, or combinations thereof. The difference effect of the stimulus on the cell-signaling of the cellular target comprises comparing the dynamic mass redistribution of the cell-signaling of the cellular target in the presence and in the absence of the stimulus. The biosensor imaging system's resolution can be, for example, from about 1 to about 50 pixels per cell, and the biosensor imaging system's resolution can be, for example, from about 1 to 10 pixels per cell at least in the perpendicular direction to the propagation direction of resonant light within the biosensor. The cell immobilized on the biosensor can be, for example, at least one of: a single cell per biosensor, or a single cluster of cells per biosensor. The immobilized live-cells on the biosensor's surface can have a confluency over a wide range, for example, from about 0.5% to about 100%, including intermediate ranges thereof. The immobilized live-cells on the biosensor's surface can also have high confluency, for example, from about 95% to about 100%. The biosensor system can comprise, for example, a swept wavelength optical interrogation system for resonant waveguide grating biosensor, imaging ellipsometry, surface plasmon resonance imaging, or combinations thereof. The biosensor output can also comprise, for example, the dynamic mass redistribution (DMR) signal. The dynamic mass redistribution signal can comprise, for example, an optical signal which comprises a measure of real time kinetics of a stimulus-induced cellular response as a function of time. Additionally or alternatively, the dynamic mass redistribution signal can comprise, for example, an optical signal which is a measure of the endpoint or multiple points of a stimulus-induced cellular response at a time point throughout a stimulation event. The biosensor output can comprise, for example, the overall dynamics, the phase, the amplitude and kinetics of the phase, and the transition time from one phase to another of the dynamic mass redistribution signal. The biosensor's optical signal can be, for example, the resonant wavelength or the resonant angle of the coupled light at each pixel or location, and which signal can depend on the image interrogation mode of the biosensor system.

In embodiments, the cellular target can comprise, for example, a feature on the cell's surface comprising, for example, at least one of a G protein-coupled receptor (GPCR), an ion channel, a receptor tyrosine kinase, a cytokine receptor, an immuno-receptor, an integrin receptor, an ion transporter, a pathogen recognition target, or combinations thereof. If desired, the cells can be patterned on the biosensor's surface using available methods. Additionally or alternatively, the cellular target can comprise, for example, an intracellular target comprising at least one of an enzyme, a kinase, a phosphatase, a monomeric or a dimeric receptor, an homologous or an heterologous receptor complex, or combinations thereof.

In embodiments, the disclosure provides a high-resolution imaging-based approach for single-cell analysis using an optical biosensor. The approach comprises the use of swept wavelength imaging optical interrogation system, as described in U.S. patent application Ser. No. 11/711,207, filed Feb. 27, 2007, entitled "Swept Wavelength Imaging Optical Interrogation System and Method for Using Same," to collect resonant wavelengths at defined locations of an optical biosensor having a cell layer at a desired confluency during a stimulatory event. This system is designed specifically for resonant waveguide grating (RWG) biosensor. The resultant optical responses, termed as dynamic mass redistribution (DMR) signals, are recorded and subsequently analyzed.

In embodiments, the disclosure provides methods that use surface plasmon resonance (SPR) imaging system for monitoring optical responses of cells at a single-cell or sub-single cell level. The SPR refers to the excitation of surface plasmons by light for planar surfaces, while localized SPR (LSPR) refers to localized surface plasmon resonance (LSPR) for nanometer-sized metallic structures. This phenomenon is the basis of many standard tools for measuring adsorption of material onto planar metal (typically gold and silver) surfaces or onto the surface of metal nanoparticles. It is behind many color based biosensor applications and different lab-on-a-chip sensors including SPR imaging. Surface plasmons are surface electromagnetic waves that propagate parallel along a metal/dielectric (or metal/vacuum) interface. Similar to RWG biosensor, SPR is also sensitive to local refractive index or its changes upon stimulation. SPR Imaging (SPRI) has been developed in the recent years and allows the monitoring localized changes in refractive index upon adsorption of molecules to the surface having patterned targets such as DNA or proteins (Smith E A, et al., "Surface Plasmon Resonance Imaging as a Tool to Monitor Biomolecular Interactions in an Array Based Format," *Appl. Spectroscopy,* 2003, 57, 320A-332A). The spatial resolution of commercially available SPRI system should allow the detection of an integrated cellular response, termed as DMR signal, at single cell or sub-single cell level, similar to the RWG biosensor imaging system.

The disclosure enables non-invasive and manipulation-free analysis of cellular responses at a single-cell level, a sub-single-cell level, or single clustered-cell level. Cells are the functional unit for all living organisms. All basic physiological functions of multicellular organisms take place or reside in the cell. The mis-regulation of cellular physiology can result in disease at the organism level. Thus, comprehending detailed cell physiology can be critical to understanding disease and providing viable cures.

Available knowledge of cell-signaling and physiology comes largely from measurement of an average cellular response upon stimulation. This is in-part due to: the limited resolution and sensitivity of most conventional technologies including cell-based assays; the difficulty preparing and handling materials from a single cell such as in vitro protein- or DNA-based analysis; and the difficulty extracting meaningful and quantifiable data for statistical analysis.

The signaling and physiology of cellular responses at the single-cell level can significantly differ from a population of cells, for example, due to their unique cellular backgrounds (i.e., context). However, conventional single-cell analysis can rely, for example, on manipulation (i.e., labels, engineering), and in many cases, requires destruction of cells (e.g., gene expression analysis). Studying cell biology and physiology at the single-cell level demands highly sensitive and high resolution assays with quantifiable and cell physiologically relevant information. To address this, label-free single-cell assays are described that possess many of the advantages of label-free optical biosensor-based cell assays for monitoring cell signaling and communication in cells, and screening compounds that alter cellular physiology at the single-cell level. In embodiments, the disclosure provides single-cell diagnostic methods for drug screening of, for example, low-growth cells (e.g., primary cells), and highly differentiated cells (e.g., stem cells during differentiation).

Although many physiological processes can be studied using one or more cell populations, others physiological processes occur either on a short timescale (e.g., kinase signaling cascades) or non-synchronously (e.g., response to an external chemical gradient). The signaling and physiology of cellular responses at the single-cell level may significantly differ from a population of cells due to cell's unique cellular backgrounds (i.e., context). Thus, taking a population average will typically not lead to an understanding of how particular cellular events occur or how particular cellular machineries function. In addition, many diseases, such as cancer, may begin with a single cell. Thus, if one hopes to find, for example, a rare mutation among populations of cells that signal the inception of a disease, then cells must be examined individually. Therefore, understanding and optionally control of many biological processes can benefit from the ability to analyze the content and molecular biology of a single cell.

Probing behavior at the single-cell level, however, is a very challenging task primarily because of the small sample volume, the typically limited abundance of material, and the fragile nature of the cell itself. Analyzing the contents of a single cell requires sensitive detection techniques and handling procedures that do not stress or damage the cell. Additionally, a proper blank or control is usually not readily available so true quantitative studies are difficult. Today, there are only a few systems that enable direct intrinsic studies of single cells and include, for example, capillary electrophoresis (CE), flow cytometry, and lab-on-a chip. These systems are based upon conventional technologies and instrumentation; they can provide only limited information about the cell content and do not present a general method for single-cell analysis. Unfortunately, these methods all rely on either labels (e.g., cytometry or lab-on-a-chip), or amplification (e.g., PCR (Polymerase Chain Reaction)), or even destruction of cells (e.g., gene profiling of single cells using electrophoresis and lab-on-a-chip). All these methods also suffer from limited means to manipulate fluids and cells. For example, Waters used microstructures to lyse single cells, followed by PCR and CE for the analysis of cellular DNA (Waters, et al., "Microchip device for cell lysis, multiplex PCR amplification, and electrophoretic sizing," *Anal. Chem.*, 1998, 70:158-162).

The disclosure provides a sensitive and non-invasive method for live-cell interrogation and analysis that uses a label-free optical biosensor and mass redistribution within the cells adherent on a biosensor surface. Precise control over the assembly of the cell arrays, such as cell patterning, can provide an additional useful aspect in embodiments of the disclosed cell-based sensors and assay methods. The methods and article of the disclosure can provide valuable insights into single cells which can be useful, for example, in advanced chemical biology, cell biology, disease diagnosis, and like applications.

Micropatterning of different types of cells on a surface is a valuable technique for controlling cellular growth, developing high throughput cell-based assays, tissue engineering, and designing bioelectronic devices. Cell arrays or cell patterning can be achieved by state-of-the-art means, primarily through cell culture and microfabrication technologies such as photolithographic technique and soft lithography. Various strategies and devices such as micro-patterned protein and DNA surfaces, micro-wells, elastomeric stencils, microchannels, and micro-networks have been applied for this purpose. These methods typically use a means to provide one set of methods for patterning surfaces and fabricating structures with dimensions in the 1-100 micron range in ways that are useful in cell biology and biochemistry. Micro-patterned protein and DNA surfaces are inexpensive to develop and simple to use. Each method has its advantages and inherent limitations. However, the different types of cells patterned on protein and DNA microarrays need to have intrinsic differences in their adhesion properties to the substrate. This limits the available combinations of cell types. Patterning two cell types with stencils requires no surface modifications. However, it is not applicable in some micro-systems, as it requires the physical removal of the elastomeric membrane. Microchannels and micro-networks offer great flexibility in simultaneously working with multiple types of biomolecules and cells. However, the geometry of the patterns and the spacing between different cell types are limited by the constraints of the microfluidic devices. Micro-contact printing can be used to generate patterns of proteins and cells, for example, by patterning self-assembled monolayers (SAMs) of alkanethiolates on the surface of gold. Using micro-contact printing methods, it is relatively straightforward to generate patterns of adhesive proteins (e.g., fibronectin, laminin, vitronectin, etc.) on surfaces; these areas of adsorbed protein allow the selective attachment of cells.

The disclosure provides methods for single cell analysis using imaging-based optical biosensors, such as a swept wavelength optical interrogation system based on a resonant waveguide grating (RWG) biosensor, imaging ellipsometry (IE), or surface plasmon resonance (SPR) imaging techniques, in combination with mass redistribution cell assay methodologies. The disclosure provides a non-invasive, highly sensitive method for single cell analysis having high information content. Currently available technologies for single cell analysis require labels or extensive or invasive sample manipulation. For example, for single cell analysis using capillary electrophoresis (CE) and gene profiling, the single cells are typically subject to lysis, and in many cases may require sample amplification (such as PCR). Flow cytometry and lab-on-a-chip approaches typically use labels to visualize specific cellular targets in a single cell. Conventional single cell assays typically measure one specific class of cellular targets (e.g., genes or proteins) at a specific period of time after stimulation. Kinetic information is largely absence. The present disclosure uses measurement of real time kinetics of stimulus-induced cellular responses, referred herein as the dynamic mass redistribution (DMR) signal. Because of the integrated nature of DMR signals, many cellular events that are mediated by a stimulus can be analyzed. Example analyses are illustrated and demonstrated in embodiments of the disclosure for three different signaling receptor classes. In embodiments, the methods of the disclosure are particularly suitable for cell signaling analysis and can be broadly applied to many classes of cellular targets including, for example, receptor tyrosine kinases, GPCRs, ion channels, viral infection, and like biological systems.

Optical Biosensor-Based Imaging

Optical biosensors generally employ a biosensor to monitor the binding of target molecules in a sample to receptors immobilized on the surface of the biosensor. The binding signal obtained typically represents an average response due to the binding at a defined area, as predetermined by the size of illuminated light (e.g., 200 microns) as well as the distance of the propagation length of coupled light traveling within the biosensor (e.g., about 200 microns for RWG biosensor). Several classes of optical biosensor systems are available that are capable of imaging, at high resolution, the binding of target molecules in a sample to an immobilized receptor. These systems include, for example, an SPR imaging system, ellipsometry imaging, and RWG imaging.

Surface Plasmon Resonance (SPR) is an optical method that can be used to monitor molecular events on surfaces. Under proper conditions, photons in a light beam and incident upon a glass-gold interface "resonate" with the electrons in the gold. As a result, instead of the light simply reflecting off the gold surface, photon energy is converted to a wave of "plasmons" in the gold. Under ideal conditions, very little light is reflected. The resonance is achieved by "coupling" the photons to the electrons in the metal using either a prism or grating. SPR can be used to detect events on a surface because adding material to the surface changes the resonance, thereby changing the percent of light reflected. Traditional instruments determine the shift in "SPR angle" (angle of minimum reflectivity) when material adsorbs to the surface. However, SPRimager® II (GWC Technologies Inc) uses prism-coupled SPR, and takes SPR measurements at a fixed angle-of-incidence, and collects the reflected light with a CCD camera. Changes on the surface are recorded as reflectivity changes. Thus SPR imaging collects measurements for all elements of an array simultaneously.

Ellipsometry can also be accomplished as imaging ellipsometry by using a CCD camera as a detector. This provides a real time contrast image of the sample, which can provide information about film thickness and refractive index. Advanced imaging ellipsometry operates on the principle of classical null ellipsometry and real-time ellipsometric contrast imaging, using a single-wavelength ellipsometer setup with a laser light source. The laser beam gets elliptically polarized after passing a linear polarizer and a quarter-wave plate. The elliptically polarized light is reflected off the sample, passes an analyzer and is imaged onto a CCD camera by a long working-distance objective. Analysis of the measured data with computerized optical modeling leads to a deduction of spatially resolved film thickness and complex refractive index values.

Corning Incorporated has also disclosed a swept wavelength optical interrogation system based on RWG biosensor for imaging application (see the abovementioned U.S. patent application Ser. No. 11/711,207). In this system, a fast tunable laser source is used to illuminate a sensor or an array of RWG biosensors in a microplate format. The sensor spectrum can be constructed by detecting the optical power reflected from the sensor as a function of time as the laser wavelength scans, and analysis of the measured data with computerized resonant wavelength interrogation modeling results in the construction of spatially resolved images of biosensors having immobilized receptors or a cell layer. The use of image sensors leads to an imaging-based interrogation scheme where two-dimensional label-free images can be obtained without moving parts.

In general, interferometric sensors are less sensitive than the evanescent wave sensors in spite of their higher spatial resolution. Evanescent wave sensors include surface plasmon resonance (SPR) and waveguide grating coupler (WGC) sensors. Photonic crystal biosensor is a waveguide grating coupler sensor or a resonant waveguide grating biosensor. In general, label-free imaging methodologies are generally still in their infancy. New techniques are being developed to realize SPR imaging (SPRI) without having to scan the wavelength or angle. However, SPRI has been limited to small size sensor chips, which are incompatible with standard microplate formats.

FIG. 1 shows a swept wavelength optical interrogation system (100). This system resembles some aspects of related spectral imaging techniques where images of an object are acquired at a sequence of different wavelengths. Each pixel of the spectral images contains a sensor spectrum, resulting in a virtual channel. Referring to FIG. 1, the system consists of several main components, including a tunable laser (110) for illuminating the biosensor (120) in a swept wavelength fashion, such that each biosensor within the array can be illuminated simultaneously, although the resonant wavelengths may differ from sensor to sensor within the array. The laser is passed through illumination optics (130) such that the laser beam is expanded, such as greater than 130 millimeters, to illuminate a portion of the entire sensor area. A wavelength referencing interferometer (140) is used to dynamically measure the laser wavelength. A high-speed digital camera (150), such as a CMOS, that contains an area-scan image-sensor with digitized outputs, is used to record the spectral images as the tunable laser scans the wavelength. Imaging optics (160), having a multi-element lense, such as a telecentric imaging lense having a field of view greater than, for example, about 130 millimeters, images the illuminated sensor area into the digital camera. Such system can be operated in two different imaging modes: the entire array of biosensors (e.g., 384 well RWG biosensor microplate) or a subset of the array of biosensors (e.g., a single sensor, or a portion of a single sensor in a 384 well biosensor array microplate). The switching of the modes can be achieved by changes of magnification of the imaging optics (160) such that it either covers the whole sensor array or focuses on the single sensor. The first imaging mode enables the large scale of measurements of cellular responses upon stimulation, particularly useful for compound screening and drug discovery. This mode monitors an averaged response from a population of cells, which can be accomplished through real time kinetic measurements or discontinuous multiple points or endpoint measurements. The second imaging mode enables the large scale of measurements of a population of cells within a single sensor or well at single cell or sub-single cell level. The resultant images from an array of sensors or a single sensor are digitized (i.e., pixelated). Each pixel represents the cellular response from a defined area as determined by its dimension and the system resolution.

Figure 2A:
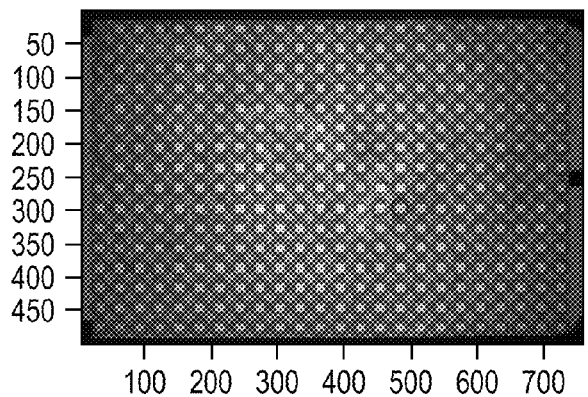
FIGS. 2A and 2B show two operational modes for different microtiter plate images at different resolutions, in embodiments of the disclosure.
Figure 2B:
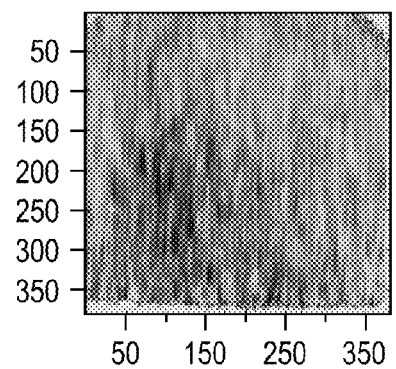

FIGS. 2A and 2B show two imaging operational modes of the disclosure. FIG. 2A shows a low resolution image at a whole or partial microtiter plate level. The image shows an entire 384 well Corning Epic® biosensor microplate. The image was obtained using the CCD camera-based swept wavelength optical interrogation system of FIG. 1. The image resolution was 750 pixels×500 pixels for the whole plate, so that for each sensor the image resolution was estimated to be about 20×20 pixels. FIG. 2B shows a high resolution image of a single well at the microtiter plate level of the swept-wavelength imaging optical interrogation system. The FIG. 2B shows the real resonant image of a single Epic® biosensor using such system at high spatial resolution (multicolor density scale not shown). The biosensor has a layer of human epidermoid carcinoma A431 cells, which is at high confluency (about 100%). At such high confluency, the average size of A431 cells is about 10 microns in diameter, as measured by confocal fluorescence imaging (data not shown). As the confluency decreases, the cells tend to spread, resulting in the increase in cell size. The image was obtained using the transverse magnetic (TM) mode from a whole RWG biosensor having a dimension of 2 mm×2 mm, with an image resolution of 380 pixel×380 pixel. From light microscopy imaging, the total numbers of cells being imaged and analyzed was about 180×180 (or about 32,400 cells). Therefore, with such spatial resolution, there were about 2×2 pixels per cell, which means that the response of each pixel represents the cellular responses from only a portion of a single cell. The resolution at the x-axis is limited by the pixel size of the CCD camera (e.g., about 6 microns). However, the spatial resolution at the y-axis, the direction which is parallel to the propagation direction of the coupled light traveling within the waveguide thin film, is much lower (e.g., about 200 microns). This is because the coupled light propagates within the waveguide thin film, and will eventually leak out the film and reflect back. The system records the wavelength of the reflected light and uses its changes as readouts for monitoring the changes in mass within sensing volume. Nonetheless, this spatial resolution enables analysis of cellular responses at single-cell or sub-single cellular levels, at least at the x-direction. Alternatively, a transverse electric (TE) mode can be used to image the cellular responses from cells within a sensor or a sensor well. The TE mode can lead to improved spatial resolution at the y-axis (i.e., the direction that the light propagates) due to the short propagation distance of resonant light when a TE mode is selected. The resolution at the y-axis using the TE mode can reach about 10 to about 20 microns (data not shown), comparable to the dimensional resolution of many types of individual cells. This measurement therefore effectively provides an integrated and resolved DMR response from a single cell or its equivalent. TE-mode imaging can be achieved by rotating the whole-plate plane relative to the incident light, or by using incident light having a relatively low wavelength.

Mass Redistribution Cell Assay Technologies (MRCAT)

Mass Redistribution Cell Assay Technologies (MRCAT) is a novel method to probe cellular responses using a refractive-sensitive optical biosensor, particularly a resonant waveguide grating (RWG) biosensor. MRCAT utilizes a label-free and non-invasive optical biosensor, specifically its evanescent wave, to monitor stimulus-induced dynamic mass redistribution (DMR) within the bottom portion of cell layer at or near the biosensor surface. The DMR signals measured are those within the detection zone (or sensing volume) of the biosensor, as determined by the short penetration of the biosensor. The biosensor exploits an evanescent wave to detect stimulus-induced alterations of the cell layer at or near the sensor surface. The evanescent wave is an electromagnetic field, created by the total internal reflection of guided light at a solution-surface interface, with a well-characterized short penetration depth, also termed as sensing volume or detection zone. Based on the sensor configuration and the physical properties of cells, the penetration depth is found to be around 150 nm for the $TM_0$ (transverse magnetic orp-polarized) mode, and about 100 nm for the $TE_0$ (transverse electric mode), meaning that the biosensor only senses the bottom portion of the cell layer. When a reverse waveguide configuration as described in (Horvath, R., et al. "Reverse-symmetry waveguides: theory and fabrication," *Applied Physics B-Lasers and Optics*, 2002, 74 (4-5): 383-393), the penetration depth can be several hundreds of nanometers (e.g., about 500 nm). Such system or configuration can be also used according to the present disclosure.

A stimulus-induced change in effective refractive index (i.e., the detected signal, $\Delta N$) is, to first order, directly proportional to the change in refractive index of the bottom portion of cell layer as expressed by equation (1):

$$\Delta N = S(C) \Delta n_c \quad (1)$$

where $S(C)$ is the sensitivity to the cell layer, and $\Delta n_c$ is the stimulus-induced change in local refractive index of the cell layer sensed by the biosensor. The $\Delta n_c$ value is directly proportional to change in local concentrations of cellular targets or molecular assemblies within the sensing volume. This is because of a well-known physical property of cells—the refractive index of a given volume within cells is largely determined by the concentrations of bio-molecules, mainly proteins, which is the basis for the contrast in light microscopic images of cells.

The detected signal ($\Delta N$) is a sum of mass redistribution occurring at distinct distances away from the sensor surface, each with unequal contribution to the overall response. This is because of the exponentially decaying nature of the evanescent wave. Taking the weighed factor $\exp(-z_i/\Delta Z_c)$ into account, the detected signal occurring perpendicular to the sensor surface is governed by the formula (2):

$$\Delta N = S(N) \alpha d \sum_i \Delta C_i \left[ e^{\frac{-z_i}{\Delta Z_C}} - e^{\frac{-z_i+1}{\Delta Z_C}} \right] \quad (2)$$

where $\Delta Z_c$ is the penetration depth into the cell layer, $\alpha$ is the specific refraction increment (about 0.0018/100 mL/g for proteins), $z_i$ is the distance where the mass redistribution occurs, and d is an imaginary thickness of a slice within the cell layer. Here the cell layer is divided into an equal-spaced slice in the vertical direction.

Thus, the detected signal, in terms of wavelength or angular shifts, is primarily sensitive to the vertical mass redistribution. Because of its dynamic nature, it is also referred to as a dynamic mass redistribution (DMR) signal. Beside the DMR signal, the biosensor is also capable of detecting horizontal (i.e., parallel to the sensor surface) redistribution of cellular contents.

When a ligand or stimulus is specific to a receptor expressed in a cell system, the ligand-induced DMR signal is also receptor-specific, dose-dependent, and saturable.

The DMR signal also exhibits expected desensitization patterns upon repeated stimulation with GPCR ligands. Desensitization and re-sensitization is common to all GPCRs. The DMR signal also maintains the fidelity of GPCR ligands, similar to those obtained using conventional methods. The biosensor can distinguish full agonists, partial agonists, inverse agonists, antagonists, and allosteric modulators.

Taken together, MRCAT studies support the hypothesis that the DMR is a novel physiological response of living cells.

In embodiments, the disclosure provides a method for non-invasive single cell analysis or interrogation using an optical biosensor imaging system. A live-cell can be, for example, directly cultured onto the surface of an optical biosensor, or alternatively can be allowed to interact with the surface of an optical biosensor. In embodiments, the interaction of a live-cell with the optical biosensor surface can be achieved with, for example, the cell's surface molecule(s) interacting with an antibody immobilized on the sensor's surface, or achieved by covalently coupling of a reactive functional group(s) anchored to the sensor's surface with the cell's surface molecule(s), for example, an amine-reactive sensor surface group(s) interacting with the amine-presenting cell surface molecule(s) such as proteins, receptors, or like entity.

The cell confluency level can be high, low, or intermediate values or ranges thereof, for example, the live-cell immobilized on the biosensor's surface can have confluencies of from about 0.5% to about 100%, depending upon, for example, the selected application(s), and the properties of selected cell. Thus, for example a selected cell type may need to communicate with or otherwise signal (such as by chemical means or physical contact means) a neighboring cell for appropriate growth, differentiation, or both. Cell cultures at high-confluency, such as from about 80% to about 100%, can typically be used to conduct and achieve so-called average cellular responses, which can benefit high-throughput screening or high-content screening. Cell cultures at high-confluency can also be used to calculate cellular status-dependent responses, such as illustrated, for example, in FIGS. 9 and 15 discussed below. Cells at low-confluency, such as from about 0.5% to about 20%, can be particularly useful for primary cells or stem cells or tissue, where long-term culturing may be difficult or is desirably avoided, since these cells types have been typically slow in growth or differentiation. Intermediate confluency, such as from about 20% to about 80%, can be selected in embodiments if desired.

The cell cultures can be, for example, adherent cells or suspension cells, depending on their conditions for adherency to achieve appropriate growth. Consequently, appropriate surface chemistries and culture conditions may need to be selected. The cell cultures can also be, for example, transformed cell lines, immortalized cells, primary cells, stem cells, tissue, or like cell cultures.

The imaging biosensor can be, for example, an SPR imaging system, an ellipsometry imaging system, a swept wavelength optical interrogation imaging system, or like imaging system.

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

Example 1

Cell culture on biosensor surface and RWG imaging assays For cell culturing, human epidermoid carcinoma A431 cells (American Type Cell Culture) were grown in Dulbecco's modified Eagle's medium (DMEM) supplemented with 10% fetal bovine serum (FBS), 4.5 g/liter glucose, 2 mM glutamine, and antibiotics. To achieve high confluent cell monolayers, about $1.8 \times 10^4$ cells at passage 3 to 8 suspended in 50 μl the DMEM medium containing 10% FBS were placed in each well of a 384 well microplate, and were cultured at 37° C. under air/5% $CO_2$ for ~1 days, followed by ~20 hr starvation through continuously culturing in the serum-free DMEM. Alternatively, to achieve low confluent cells 1000 cells were added to each well, followed by the same cell culture conditions. For RWG imaging system, a swept wavelength interrogation system was built in house, according to U.S. patent application Ser. No. 11/711,207 (Corning Inc.). In this system, a fast tunable laser source is used to illuminate a sensor or an array of RWG biosensors in a microplate format. The sensor spectrum can be constructed by detecting the optical power reflected from the sensor as a function of time as the laser wavelength scans, and analysis of the measured data with computerized resonant wavelength interrogation modeling results in the construction of spatially resolved images of biosensors having immobilized receptors or a cell layer. The images were obtained for a single sensor (i.e., a single well of a 384-well RWG biosensor microplate). Epic 384 well cell assay microplates were obtained from Corning Inc (Corning, N.Y.). The microplates, in which each well consists of a resonant waveguide grating (RWG) biosensor, are ready-to-culture and used directly without any pretreatments.

For kinetic assays, the cells were washed with HBSS (Hanks Balanced Salt Solution with 20 mM HEPES) buffer. After 1 hour incubation within the detection system, a single sensor well was imaged for a given period of time (e.g., 5 min) to establish a baseline response. Then, a compound solution was transferred into the well using a pipette, the cellular response was then recorded continuously for another period of time. The lid of the sensor microplates was on most of the time throughout the assay, except of a short period of time (about 30 seconds) when the compound was introduced. All studies were carried out at room temperature (21° C.).

Data analysis was carried out using MATLab software. Multiple parameter analysis was carried out following appropriate models. From the kinetic profiles of a ligand-induced response for a given pixel, six parameters can be extracted, including the resonant wavelength, the overall dynamics, the phases (P-DMR, N-DMR, net-zero DMR), the amplitudes of these DMR phases or events, the kinetics of each DMR event, and the transition time from one phase to another. Correlation analysis among different combinations of these parameters, in addition to the location of the pixel, gave rise to extremely useful information regarding to the homogeneity or heterogeneity of cellular responses, and the underlying cellular mechanisms to account for these DMR events.

Example 2

Single-cell analysis of epidermal growth factor (EGF) receptor (EGFR) signaling EGF receptor belongs to the family of receptor tyrosine kinases. EGF binds to and stimulates the intrinsic protein-tyrosine kinase activity of EGFR, which in turn initiates signal transduction cascades, principally involving the MAPK, Akt, and JNK pathways. Upon EGF stimulation, there are many events that can lead to mass redistribution in A431 cells in such a cell line endogenously over-expressing EGFRs. It is known that EGFR signaling depends on cellular status. As a result, the EGF-induced DMR signals also depend on the cellular status. In quiescent cells obtained through 20 hour culturing in serum-free medium, EGF stimulation leads to a DMR signal with three distinct and sequential phases: (i) a positive phase with increased signal (P-DMR), (ii) a transition phase, and (iii) a decay phase (N-DMR) (FIG. 3).

FIGS. 2A and 2B show two operational modes of the swept-wavelength imaging optical interrogation system. FIG. 2A images a whole 384-well RWG biosensor microplate, at relatively low resolution for each sensor embedded within the bottom of each well. FIG. 2B images a biosensor at high resolution, which is located within the bottom of a well. In embodiments the disclosure the single-cell analysis prefers the high-resolution operational mode, where the spatial resolution is, for example, about 6 microns in the direction perpendicular to the propagation direction of the coupled light (i.e., the x-axis), and about 200 microns in the direction parallel to the propagation direction of the coupled light (i.e., the y-axis). Since the average size of cells is about the same or greater than the spatial resolution at the x-axis, such imaging system enables single cell or sub-single cell analysis (multicolor density scale not shown).

Chemical biology and cell biology studies show that the EGF-induced DMR signal is primarily linked to the Ras/MAPK pathway, which proceeds through MEK and leads to cell detachment. Two evidences suggest that the P-DMR is mainly due to the recruitment of intracellular targets to the activated receptors at the cell surface. First, blockage of either dynamin or clathrin activity has little effect on the amplitude of the P-DMR event. Dynamin and clathrin, two downstream components of EGFR activation, play crucial roles in executing EGFR internalization and signaling. Second, the blockage of MEK activity partially attenuates the P-DMR event. MEK is an important component in the MAPK pathway, which first translocates from the cytoplasm to the cell membrane, followed by internalization with the receptors, after EGF stimulation.

In contrast, the N-DMR event is due to cell detachment and receptor internalization. Fluorescent images show that EGF stimulation leads to significant numbers of receptors internalized and cell detachment. It is known that blockage of either receptor internalization or MEK activity prevents cell detachment, and receptor internalization requires both dynamin and clathrin. This suggests that blockage of either dynamin or clathrin activity should inhibit both receptor internalization and cell detachment, while blockage of MEK activity should only inhibit cell detachment, but not receptor internalization. As expected, either dynamin or clathrin inhibitors completely inhibit the EGF-induced N-DMR (about 100%), while MEK inhibitors only partially attenuate the N-DMR (about 80%). Fluorescent images also confirm that blocking the activity of dynamin, but not MEK, impairs the receptor internalization.

Figure 3A:
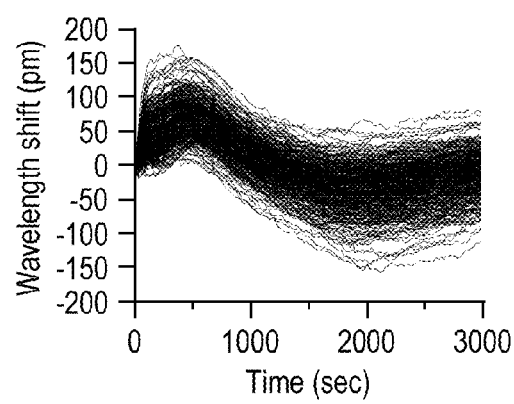
FIGS. 3A and 3B, respectively, show kinetic responses of quiescent A431 cells, at the single-cell level or sub-single cell level, and at a high cell population level after stimulation, in embodiments of the disclosure.
Figure 3B:
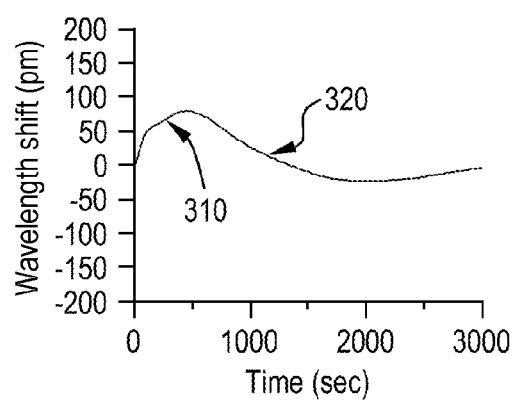

FIGS. 3A and 3B show kinetic responses of quiescent A431 cells after stimulation with 32 nM epidermal growth factor, at the single-cell level or sub-single cell level, and at a high-cell population level, respectively. The high-cell population level represents an averaged response of, for example, about several tens of thousands of cells. FIG. 3A shows representative kinetic profiles of A431 cells located within a row of 380 pixels across the entire RWG biosensor whose dimension is 2 mm×2 mm. Each kinetic profile represents approximately a single-cell response at each pixel. FIG. 3B shows the average response of cells adherent on the area of these 380 pixels. Since the cell confluency is around 100%, the average size of cells is about 10 micrometers in diameter, and the numbers of cells are about 200 within a row across the sensor. The indicated regions are P-DMR (310) and the N-DMR (320).

FIGS. 4A and 4B show two sequential resonant wavelength images of an entire biosensor having a layer of quiescent A431 cell at about 100% confluency in response to stimulation with 32 nM epidermal growth factor (multicolor density scales not shown). FIG. 4A shows an image of the net change in resonant wavelength before stimulation, which indicates that there is no change in resonant wavelength during 10 minutes continuous monitoring. FIG. 4B shows an image of the net change in resonant wavelength 10 minutes after stimulation with 32 nM EGF. The contrast in FIG. 4B shows the differential response of a cell at each location upon stimulation.

FIGS. 5A and 5B show aspects of the distribution of quiescent A431 cell responses upon stimulation with 32 nM EGF. FIG. 5A shows the distribution of the amplitudes (Response Units) of P-DMR events. FIG. 5B shows the distribution of the amplitudes (Response Units) of N-DMR events. These results illustrate that the DMR signals mediated by EGF-triggered EGFR activation in A431 cells can have a wide distribution and can be heterogeneous, possibly due to the difference in cellular states, such as, cell cycle, cell quiescent state, or adhesion degree. These results also suggest that the EGF receptor signaling mediated by EGF is dependent on cellular status.

Example 3

Single cell analysis of bradykinin $B_2$ receptor signaling Bradykinin $B_2$ receptor is endogenously expressed in A431 cells. In A431 cells, $B_2$ receptor primarily mediates signaling through its coupled $G_q$ proteins. Unique to $G_q$-coupled receptor signaling is the dramatic translocation of its signaling components, including several protein kinase C (PKC) isoforms, GPCR kinase, β-arrestin, PIP (phosphatidylinositol phosphate)-binding proteins, and diacylglycerol-binding proteins, to name but a few. Following receptor biology, our numerical analysis suggests that the protein translocation and receptor internalization are two primary resources for the DMR signatures observed for $G_q$-coupled receptor signaling (Fang, Y., et al., *Biophys. J.*, 2006, 91, 1925-1940).

Figure 6A:
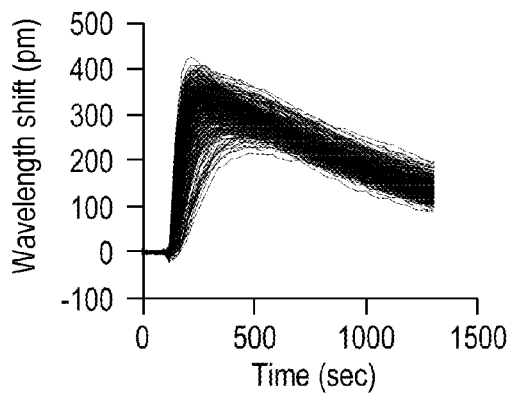
FIGS. 6A and 6B, respectively, show kinetic responses of quiescent A431 cells, A) at single/sub-single cell level; and B) at large populations of cells level, before and after stimulation with 16 nM bradykinin, in embodiments of the disclosure.
Figure 6B:
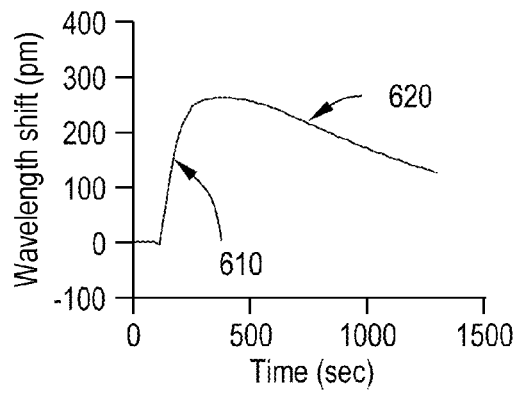

FIGS. 6A and 6B show kinetic responses of quiescent A431 cells before and after stimulation with 16 nM bradykinin. FIG. 6A shows kinetic responses of A431 cells within a representative row across the biosensor, i.e., 380 pixels located within the same row (i.e., x-axis in FIG. 2B) across an entire sensor. The solid arrow in FIG. 6A indicates the time when bradykinin was introduced. FIG. 6B shows the average response of cells adherent on the area of these 380 pixels. Again, since the cell confluency is around 100%, and since the average size of cells is around 10 microns in diameter, and since the number of cells is around 200 within a row across the sensor, each kinetic profile in FIG. 6A represents approximately a single-cell response at each pixel. The bradykinin-induced DMR signals consist of two phases: an initial rapid P-DMR (610) and a subsequent N-DMR (620).

Figure 7A:
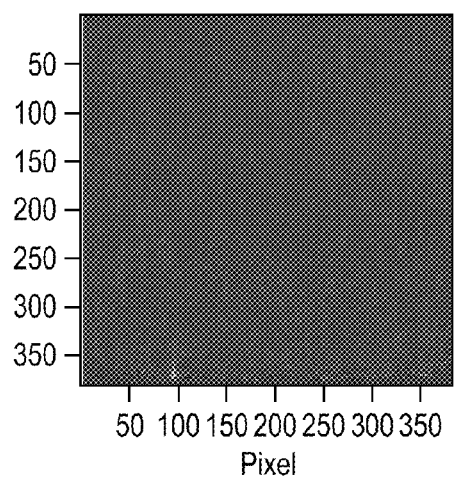
FIGS. 7A and 7B, respectively, show sequential resonant wavelength images of a biosensor having quiescent A431 cell layer at about 100% confluency: A) before and B) after stimulation with 16 nM bradykinin, in embodiments of the disclosure.
Figure 7B:
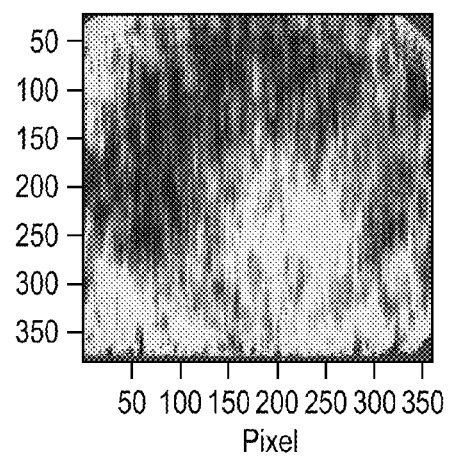

FIGS. 7A and 7B show two sequential resonant wavelength images of an entire biosensor having a layer of quiescent A431 cells at about 100% confluency in response to stimulation with 16 nM bradykinin (multicolor density scales not shown). FIG. 7A shows an image of the net change in resonant wavelength before stimulation when continuously monitored for 10 minutes. The little or no change(s) within the 10 minute interval suggests that the cells reached an equilibrium state. FIG. 7B shows an image of the net change in resonant wavelength 6 minutes after stimulation. The contrast in FIG. 7B shows the differential response of a cell at each location upon stimulation.

Figure 8A:
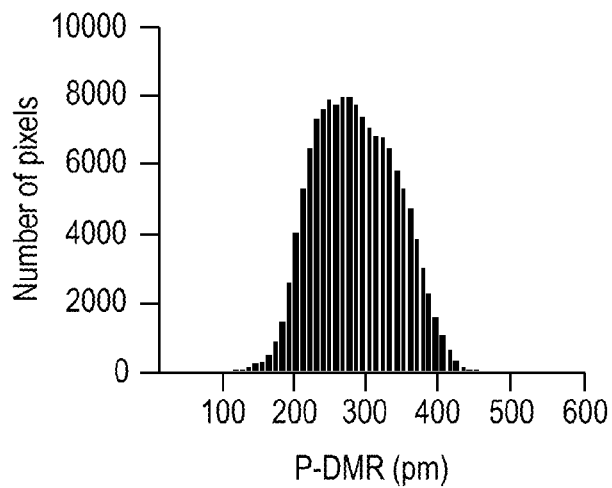
FIGS. 8A to 8C, respectively, show the distribution of quiescent A431 responses upon stimulation with 16 nM bradykinin: A) the P-DMR amplitude; B) the transition time from the P-DMR to the N-DMR; and C) the kinetics of the P-DMR, in embodiments of the disclosure.
Figure 8B:
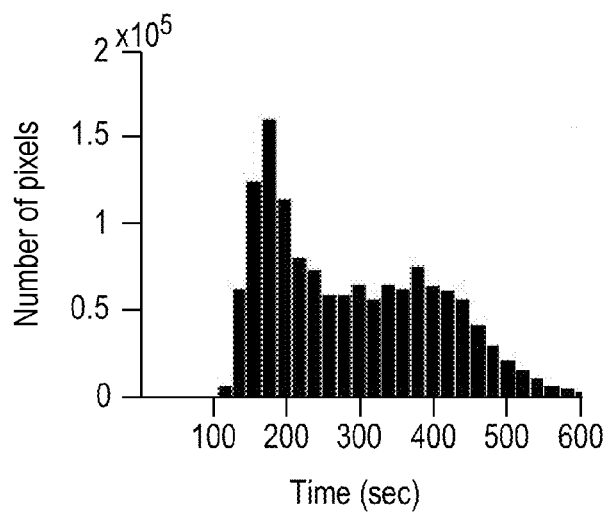
Figure 8C:
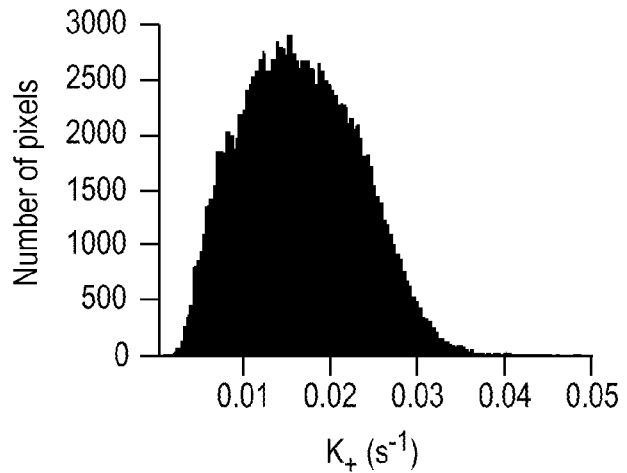

FIGS. 8A-8C show the distribution of quiescent A431 cell responses upon stimulation with 16 nM bradykinin. FIG. 8A shows a histogram of the P-DMR amplitudes. FIG. 8B shows a histogram of the transition times. Here the transition time refers to the time required for the occurring of the N-DMR (i.e., the time required for the completion of the P-DMR). FIG. 8C shows a histogram of the kinetics of the P-DMR event. The kinetics of the P-DMR was obtained by fitting the P-DMR event with a non-linear single phase exponential regression. These results demonstrate that the P-DMR amplitudes were relatively homogenous, whereas the transition time falls into two major populations. Conversely, the P-DMR kinetics were relatively heterogeneous.

Figure 9A:
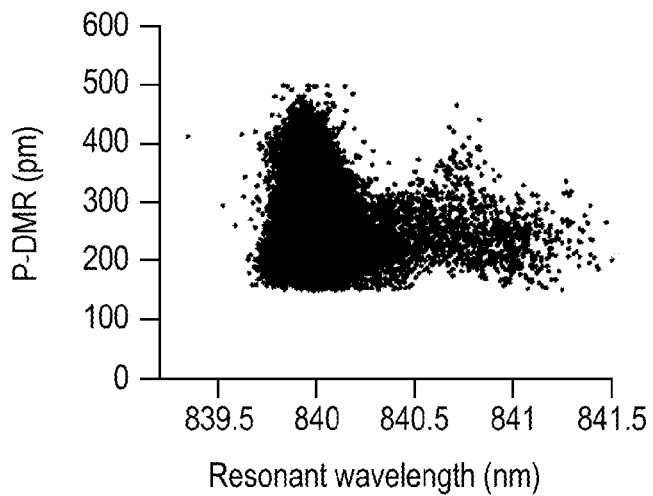
FIGS. 9A to 9C, respectively, show a correlation between the resonant wavelength at each pixel obtained before stimulation and the cellular responses at each pixel induced by 16 nM bradykinin: A) the P-DMR amplitude; B) the N-DMR amplitude; and C) the transition time, in embodiments of the disclosure.
Figure 9B:
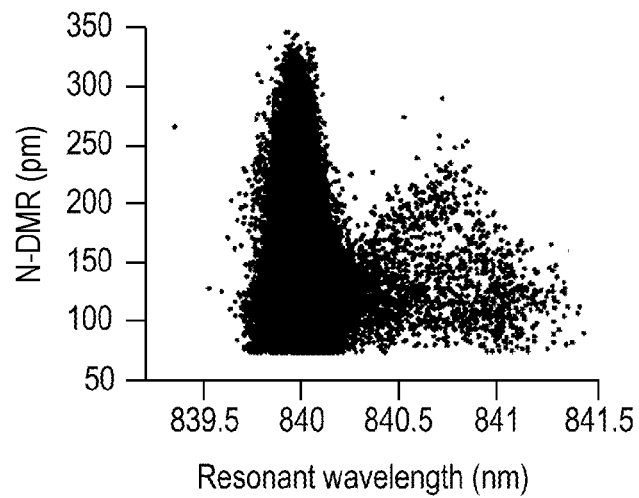
Figure 9C:
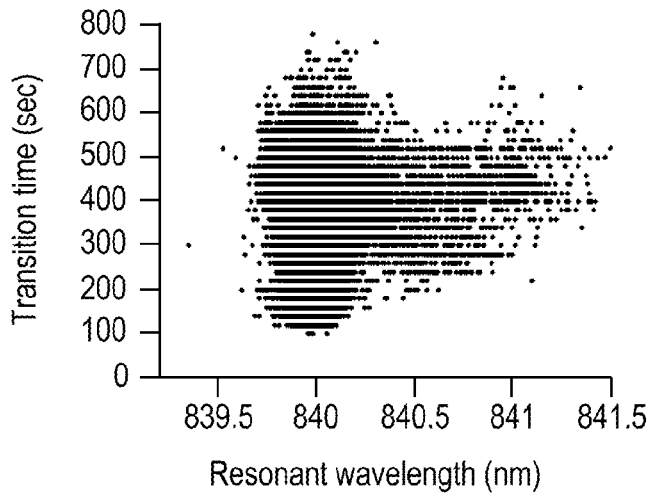

FIGS. 9A to 9C show a correlation between the resonant wavelength at each pixel obtained before stimulation and the cellular responses at each pixel after stimulation. FIG. 9A shows the amplitude of the P-DMR as a function of resonant wavelength. FIG. 9B shows the amplitude of the N-DMR as a function of resonant wavelength. FIG. 9C shows the transition time to complete the P-DMR as a function of resonant wavelength. The resonant wavelength at a given pixel reflects the total mass distribution within the area of the pixel, indicating the adhesion degree and the distribution of cellular component material within the cell. Generally the higher the resonant wavelength at a given pixel is, the higher the adhesion degree is. Any of P-DMR, N-DMR, or transition time, can exhibit a complex correlation with the resonant wavelength. Although not limited by theory these results suggest that once the resonant wavelength is high enough, the cellular response is less sensitive to its local mass distribution or density. However, when the resonant wavelength is relatively low, the cellular response can be highly variable and heterogeneous.

Figure 10A:
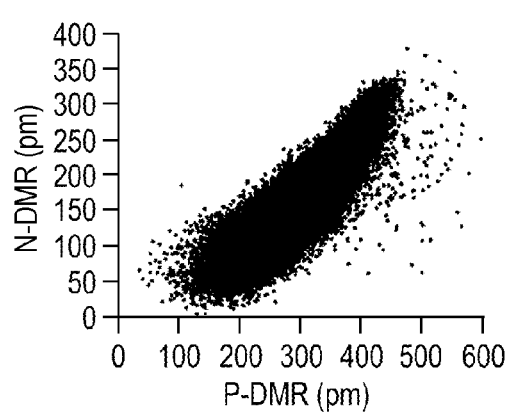
FIGS. 10A to 10D, respectively, show a correlation between the P-DMR amplitude of the kinetic response induced by 16 nM bradykinin: A) the N-DMR amplitudes; B) the integrated area of the whole response; C) the kinetics; and D) the transition time, in embodiments of the disclosure.
Figure 10B:
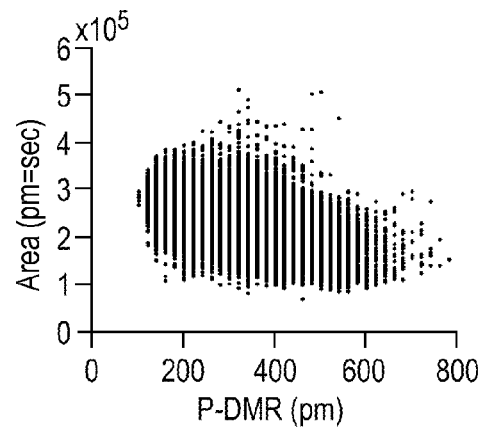
Figure 10C:
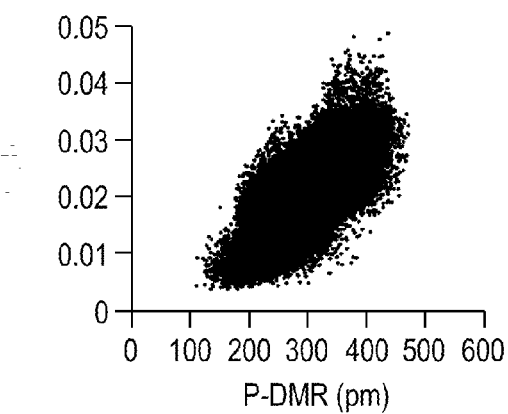
Figure 10D:
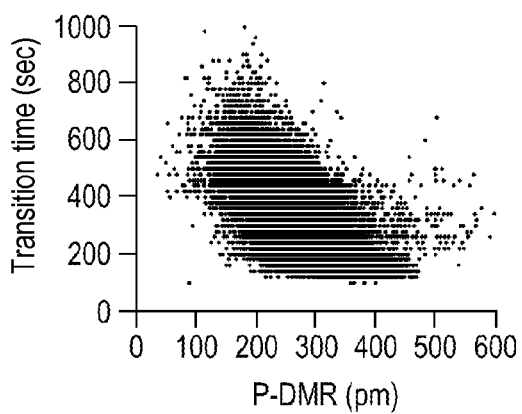

FIGS. 10A to 10D show correlations between cellular responses. FIG. 10A shows the correlation between the P-DMR and N-DMR amplitudes. The strong and positive correlation suggests that both P-DMR and N-DMR events are related each other. For example, the higher the P-DMR amplitude is, the higher the N-DMR amplitude is. FIG. 10B shows the correlation between the P-DMR amplitude and the integrated area of a response peak. The integrated area of the response peak indicates the total mass movement or rearrangement during the cellular response. The weak correlation between the integrated area and P-DMR suggests that the total mass movement upon stimulation is constant. FIG. 10C shows the correlation between the P-DMR amplitude and its kinetics. The results show that faster the kinetics produce larger P-DMR FIG. 10D shows the correlation between the P-DMR amplitude and the transition time. The results show that the bigger the P-DMR, the shorter the transition time. These correlations suggest that there may be different coupling efficiency between the receptor and its G proteins.

Figure 11:
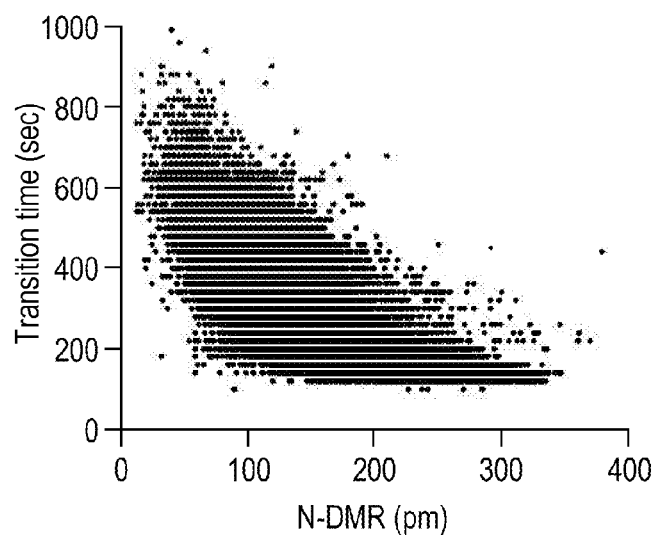
FIG. 11 shows a correlation between the N-DMR amplitude and the transition time in the cell response induced by 16 nM bradykinin, in embodiments of the disclosure.

FIG. 11 shows the correlation between the N-DMR amplitude and the transition time. The results show that the bigger the N-DMR, the shorter the transition time.

Together, these correlations suggest that many downstream cellular events that account for the DMR signal induced by bradykinin or like stimulants are highly interconnected, possibly due to the regulatory mechanisms of cells that control their responses to stimulation. The difference in cellular responses at distinct pixels and their corresponding cells indicate that the cellular response at the single-cell level can be largely heterogeneous and dependent on cellular status or background of the cells.

Example 4

Single cell analysis of beta2 adrenergic receptor signaling $β_2$-adrenergic receptor ($β_2AR$) is a prototypical $G_s$-coupled receptor. Central to the $β_2AR$ signaling is sequential activation of the receptor, G protein, and adenylyl cyclase at the plasma membrane, increased accumulation of a diffusible second messenger cAMP, and activation of protein kinase A (PKA). Epinephrine results in a dose-dependent DMR signal in A431 cells, a cell line that presents large numbers of $\beta_2AR$, but not $\beta_1AR$. The DMR is characterized by a small N-DMR, followed by a significant P-DMR event. Chemical-biology studies link the epinephrine-induced DMR to the cAMP/PKA pathway. Since the majority of downstream signaling components directly involved in the $\beta_2AR$ signaling complexes are already compartmentalized at or near the cell membrane, the recruitment of intracellular targets to the activated receptors may be much less pronounced than for EGFR or for $G_q$-coupled receptor signaling. Presently known exceptions to this trend include, for example, protein kinase A (PKA) anchoring proteins (AKAPs) and $\beta$-arrestins. However, together with the rapid segregation of receptor signaling complexes into the clathrin-coated pits, the conversion of local ATP to cAMP and its subsequent diffusion away from the cell membrane compartments leads to a rapid and significant decrease in local mass. The convergence of these events is believed to lead to the initial N-DMR event. It is known that the PKA activation results in suppression of several kinases (e.g., focal adhesion kinase) involved in the cell adhesion complexes, leading to increased cell adhesion, and as confirmed by our protein microarray studies. The increase in adhesion is the major contributor to the P-DMR event.

Figure 12A:
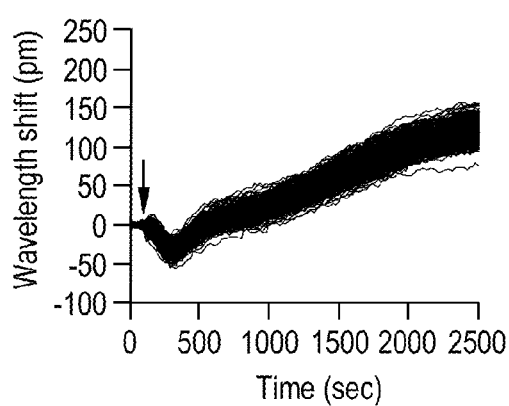
FIGS. 12A and 12B, respectively, show kinetic responses of quiescent A431 cells before and after stimulation with 2 nM epinephrine: A) at a single pixel level, and B) at a large population of cells level, in embodiments of the disclosure.
Figure 12B:
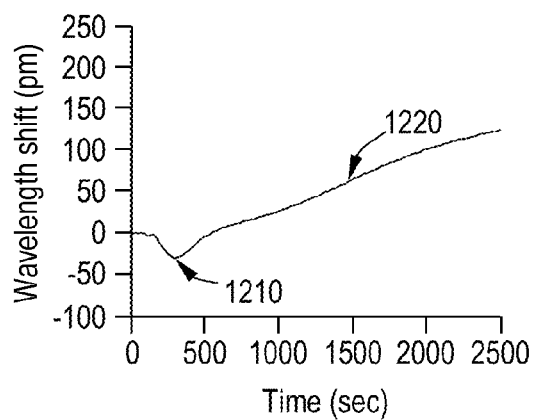

FIGS. 12A and 12B show kinetic responses of quiescent A431 cells before and after stimulation with 2 nM epinephrine. FIG. 12A shows kinetic responses of A431 cells within a representative row across the biosensor, that is, within the same row (i.e., x-axis in FIG. 2B) across an entire sensor. The solid arrow (1200) in FIG. 12A indicates the time when epinephrine was introduced. FIG. 12B shows the average response of cells adherent on the area of these 380 pixels including the N-DMR (1210) and the subsequent P-DMR (1220) (i.e., averaged signal of the cells on a single sensor).

Figure 13A:
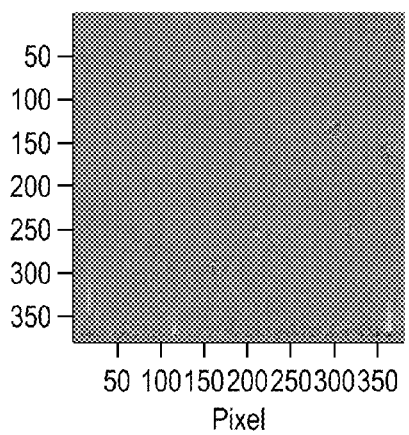
FIGS. 13A and 13B, respectively, show sequential resonant wavelength images of a biosensor having a quiescent A431 cell layer at about 100% confluency: A) before and B) after stimulation with 2 nM epinephrine, in embodiments of the disclosure.
Figure 13B:
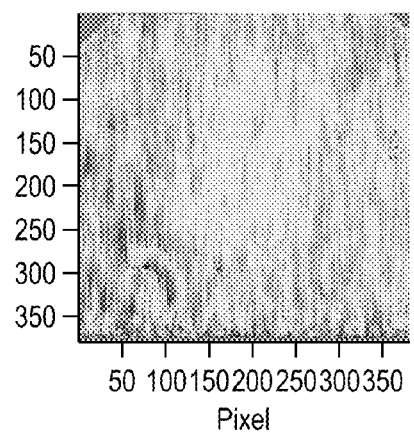

FIGS. 13A and 13B show two sequential resonant images of an entire biosensor having a layer of quiescent A431 cell at about 100% confluency in response to stimulation with 2 nM epinephrine. FIG. 13A shows an image of the net change in resonant wavelength before stimulation when continuously monitored for 10 minutes. The little or no changes during the 10 minute interval suggested that the cells reached an equilibrium state. FIG. 13B shows an image of the net change in resonant wavelength 40 minutes after stimulation. The grayscale contrast (multicolor density scales not shown) at locations in FIG. 13B indicates a differential response of a cell upon stimulation.

Figure 14A:
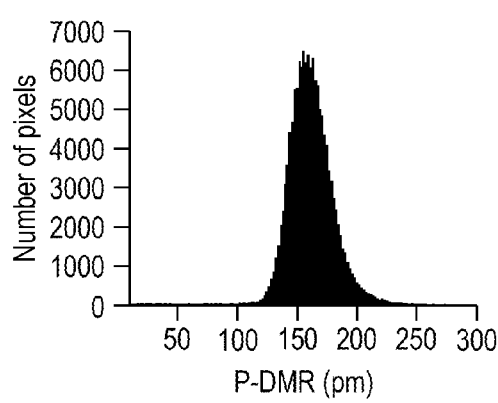
FIGS. 14A and 14B, respectively, show the distribution of quiescent A431 responses as: A) the amplitudes of P-DMR; and B) the transition time upon stimulation with 2 nM epinephrine, in embodiments of the disclosure.
Figure 14B:
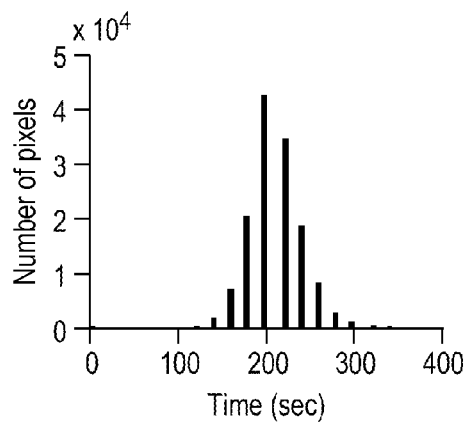

FIGS. 14A and 14B show distributions of quiescent A431 cell responses upon stimulation with 2 nM epinephrine. FIG. 14A shows the distribution of amplitudes of P-DMR events as a function of the number of pixels in thousands. FIG. 14B shows the distribution of transition times a function of the number of pixels in thousands. The results show that the DMR signals mediated by epinephrine-triggered EGFR activation in A431 cells exhibit a relatively tight distribution and are relatively homogenous.

Figure 15A:
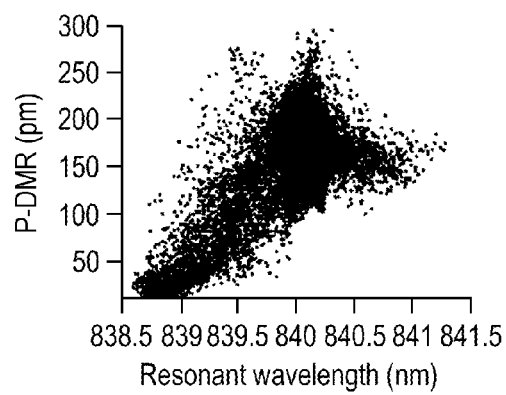
FIGS. 15A and 15B, respectively, show the correlation between the resonant wavelength at each pixel before stimulation and the cellular responses: A) the P-DMR amplitude; and B) the transition time, at each pixel after stimulation, in embodiments of the disclosure.
Figure 15B:
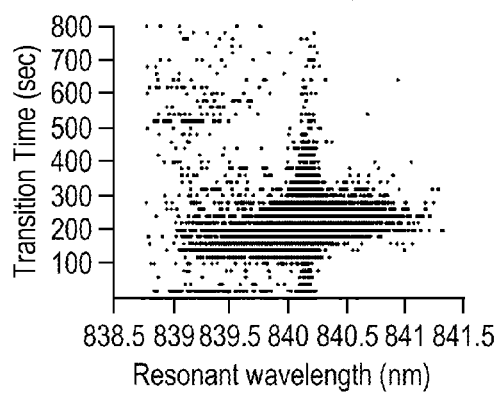

FIGS. 15A and 15B show the correlation between the resonant wavelength at each pixel obtained before stimulation and the cellular responses at each pixel after stimulation. FIG. 15A shows the amplitude of P-DMR as a function of resonant wavelength. FIG. 15B shows the transition time from the N-DMR to the P-DMR event as a function of resonant wavelength. Generally, the higher the resonant wavelength at the observed location, the higher the P-DMR amplitude, but the transition time is less sensitive to the initial resonant wavelength. Although not bound by theory, the results also suggest that there is a direct correlation between the resonant wavelength and the P-DMR.

Example 5

Single-cell analysis of Bradykinin $B_2$ receptor signaling of A431 cells in a cluster Cell signaling is dependent on cellular context (i.e., background). A431 cells tend to grow in a cluster and eventually into a monolayer under normal culture conditions. Cell signaling may differ greatly when the cell confluency varies. Here the B2 receptor signaling was examined in A431 cells cultured onto a RWG biosensor in a cluster colony format.

Figure 16A:
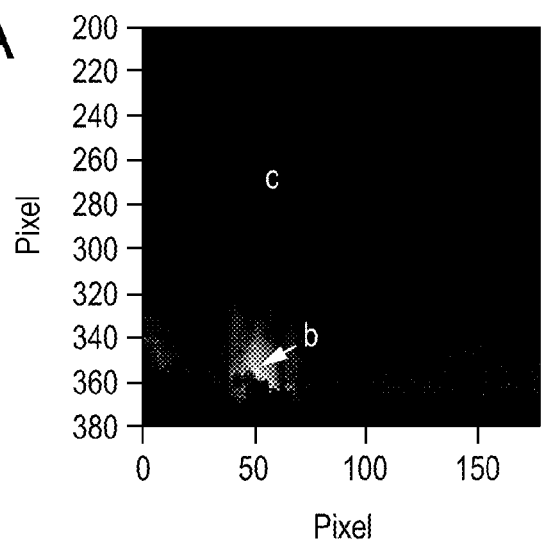
FIGS. 16A to 16C, respectively, show the resonant wavelength image of a single cluster of A431 cells on the biosensor, an average response of a large population of cells, the kinetic DMR signal of an A431 cell in a FIG. 16A cluster that was induced by 16 nM bradykinin, and a negative control response, which was obtained on the area of the biosensor having no cells, in embodiments of the disclosure.
Figure 16B:
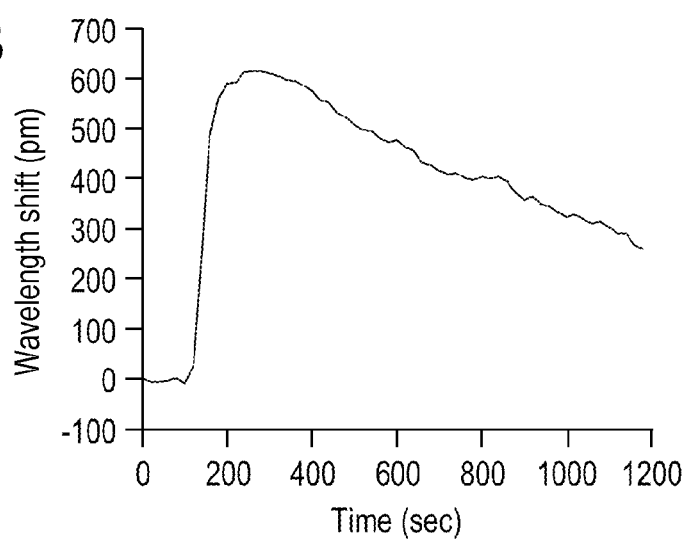
Figure 16C:
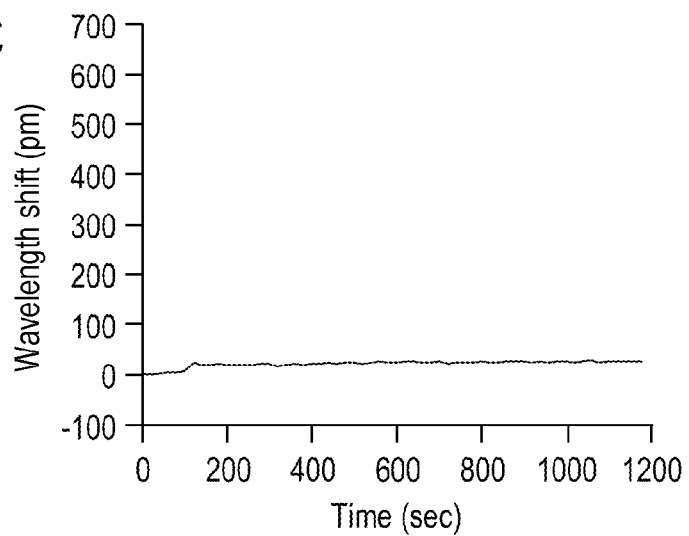

FIG. 16A shows the resonant wavelength image of the biosensor having a cluster of A431 cells 3 min after stimulation with 16 nM bradykinin. As shown in FIG. 16A (multicolor density scale not shown) there was only a single cluster of A431 cells growing on the RWG biosensor. The single cluster of A431 cells on the biosensor was confirmed with light microscope images which showed that there was a cluster of five cells (indicated by pointer "b"). FIG. 16B shows the kinetic DMR signal of an A431 cell in the FIG. 16A cluster that was induced by 16 nM bradykinin. The kinetic profile of the bradykinin response was similar to the $G_q$-type DMR signal, but with larger amplitudes compared to that in FIG. 6B. FIG. 6B is an average response of a large population of cells. FIG. 16C shows a negative control response, which was obtained on the area of the biosensor having no cells (indicated by point "c" in FIG. 16A). The results show that when there is no cell on the sensor, bradykinin does not result in any detectable response. In summary, the results shown in FIG. 16A to 16C suggest that the high resolution imaging system of the disclosure enables the detection of cellular responses induced by a ligand for a single cell, such as a single-cell or in a small-cluster format or colony.

The disclosure has been described with reference to various specific embodiments and techniques. However, it should be understood that many variations and modifications are possible while remaining within the spirit and scope of the disclosure.

REFERENCES

1. Z. H. Wang, et al., "A Label-Free Multi-sensing Immunosensor Based on Imaging Ellipsometry," *Anal. Chem.*, 75, 6119-6123 (2003).
2. C. E. Jordan, et al., "Surface plasmon resonance imaging measurements of DNA hybridization adsorption and streptavidin/DNA multilayer formation at chemically modified gold surfaces," *Anal. Chem.*, 69, 4939-4947 (1997).
3. Fang, Y., et al., (2006) *Biophys. J.*, 91, 1925-1940.
4. Fang, Y., et al., (2005) *Anal. Chem.*, 77: 5720-5725.
5. Fang, Y., et al., (2005) *FEBS Lett.*, 579: 6365-6374.
6. Fang, Y., et al., (2007) *J. Pharmacol. Toxicol. Methods*, 55, 314-322.
7. Fang, Y., (2006) *Assays and Drug development Technologies*, 4: 583-595.

What is claimed is:

1. A method for characterizing the response of live-cells a to a stimulus, the method comprising:
    contacting the live-cells immobilized on a resonance waveguide grating (RWG) biosensor with a stimulus for a selected cellular target;
    interrogating and detecting the dynamic mass redistribution (DMR) of each individual cell of the stimulus contacted live-cells using a spatially resolved swept wavelength RWG biosensor imaging system, wherein the system uses a wavelength tunable light source to illuminate and interrogate the biosensor and a digital camera to detect and record the resonant wavelength image of the RWG biosensor with a pixelated resolution less than the average size of the individual live-cells; and determining the effect of the stimulus on the cell-signaling of the cellular target in the different individual cells among the stimulus contacted live-cells.

2. The method of claim 1 wherein the live-cells comprise at least one of: an isolated single and individual cell, or a single and individual cell within a cell cluster.

3. The method of claim 1 wherein the effect of the stimulus on the cell-signaling of the cellular target in the stimulus contacted live-cells comprises comparing the dynamic mass redistribution of the cell-signaling of the cellular target in the presence and in the absence of the stimulus.

4. The method of claim 1 wherein the biosensor imaging system's pixelated resolution is from about 1 to about 50 pixels per individual live-cell.

5. The method of claim 1 wherein the biosensor imaging system's pixelated resolution is from about 1 to 10 pixels per individual live-cell at least in the direction perpendicular to the propagation direction of resonant light within the biosensor.

6. The method of claim 1 wherein each individual cell immobilized on the biosensor's surface is one of a cluster of many cells when the cells have a confluency of from about 0.5% to about 100%.

7. The method of claim 1 wherein each individual cell immobilized on the biosensor's surface is one of a cluster of many cells when the cells have a confluency of from about 80% to about 100%.

8. The method of claim 1 wherein the dynamic mass redistribution signal comprises an optical signal that measures real time kinetics of a stimulus-induced cellular response as a function of time.

9. The method of claim 1 wherein the dynamic mass redistribution signal comprises an optical signal that measures an endpoint or multiple points of a stimulus-induced cellular response over time and throughout a stimulation event.

10. The method of claim 1 wherein the biosensor imaging system provides biosensor output comprising at least one of: the overall dynamics, the phase, the amplitude and kinetics of the phase, the transition time from one phase to another of the dynamic mass redistribution signal, or a combination thereof.

11. The method of claim 1 wherein the dynamic mass redistribution is the resonant wavelength or the resonant angle of the coupled light at each pixel or location of the biosensor and which wavelength or angle depends on the image interrogation mode of the biosensor system.

12. The method of claim 1 wherein the cellular target comprises a feature on the cell's surface comprising at least one of a G protein-coupled receptor (GPCR), an ion channel, a receptor tyrosine kinase, a cytokine receptor, an immunoreceptor, an integrin receptor, an ion transporter, a pathogen recognition target, or a combination thereof.

13. The method of claim 1 wherein each individual cell immobilized on the biosensor's surface is patterned onto the surface of the biosensor.

14. The method of claim 1 wherein the interrogating and detecting the dynamic mass redistribution (DMR) is accomplished in a period of time of at least one of: from about seconds to about minutes, from about minutes to about hours, from about days to about weeks, or a combination thereof.

15. The method of claim 1 wherein the cellular target comprises an intracellular target comprising at least one of: an enzyme, a kinase, a phosphatase, a monomeric or a dimeric receptor, an homologous or an heterologous receptor complex, or combinations thereof.

16. The method of claim 1 wherein each individual cell immobilized on the biosensor comprises an adherent cell, a suspension cell, or a combination thereof.

17. The method of claim 1 wherein the effect of the stimulus on the cell-signaling of the cellular target comprises comparing the stimulus-induced dynamic mass redistribution (DMR) of the cell-signalling of the cellular target in different individual cells to determine the homogeneity or heterogeneity of cellular responses at the single and individual cell level when the biosensor surface has more than one live-cell.

18. The method of claim 17 wherein the different individual cells are a single type of cells.

19. The method of claim 17 wherein the different individual cells contain at least two different types of cells.

* * * * *